(12) United States Patent
Cohen et al.

(10) Patent No.: US 7,399,869 B2
(45) Date of Patent: Jul. 15, 2008

(54) FIBROBLAST ACTIVATION PROTEIN INHIBITOR COMPOUNDS AND METHODS

(75) Inventors: Frederick Cohen, San Francisco, CA (US); Wayne J. Fairbrother, Burlingame, CA (US); Clifford Quan, Belmont, CA (US); Daniel P. Sutherlin, South San Francisco, CA (US); Beni B. Wolf, Redwood City, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 11/437,182

(22) Filed: May 18, 2006

(65) Prior Publication Data

US 2006/0276435 A1    Dec. 7, 2006

Related U.S. Application Data

(60) Provisional application No. 60/730,292, filed on Oct. 25, 2005, provisional application No. 60/682,970, filed on May 19, 2005.

(51) Int. Cl.
C07D 207/00 (2006.01)
A01N 43/36 (2006.01)

(52) U.S. Cl. ........................ 548/405; 514/423

(58) Field of Classification Search ........................ None
See application file for complete search history.

(56) References Cited

U.S. PATENT DOCUMENTS

| | | | |
|---|---|---|---|
| 4,935,493 A | 6/1990 | Bachovchin et al. | |
| 5,288,707 A | 2/1994 | Metternich | |
| 5,574,017 A * | 11/1996 | Gutheil | 514/19 |
| 6,355,614 B1 | 3/2002 | Wallner | |
| 6,613,879 B1 | 9/2003 | Firestone et al. | |
| 6,825,169 B1 | 11/2004 | Bachovchin et al. | |
| 6,911,467 B2 | 6/2005 | Evans | |
| 2002/0155565 A1 | 10/2002 | Garin-Chesa et al. | |
| 2003/0055052 A1 | 3/2003 | Peters et al. | |
| 2003/0158114 A1 | 8/2003 | Wallner et al. | |
| 2003/0211979 A1 | 11/2003 | Blech et al. | |
| 2003/0232742 A1 | 12/2003 | Peters et al. | |
| 2004/0229820 A1 | 11/2004 | Bachovchin et al. | |
| 2006/0089312 A1 | 4/2006 | Bachovchin et al. | |

FOREIGN PATENT DOCUMENTS

| WO | WO 93/08259 | 4/1993 |
|---|---|---|
| WO | WO 93/10127 | 5/1993 |
| WO | WO 03/092605 A2 | 11/2003 |
| WO | WO 2005/047297 A1 | 5/2005 |
| WO | WO2007005991 * | 7/2005 |

OTHER PUBLICATIONS http://en.wikipedia.org/wiki/Racemic_mixture (1 page).*
Bachovchin et al., "inhibition of IgA1 proteinases from *Neisseria gonorrhoeae* and *Hmophilus influenzae* by peptide prolyl boronic acids", The Journal of Biol. Chem., 1990, 265, 3738-3743.*
http://en.wikipedia.org/wiki/Amino_acid (11 pages).*
http://en.wikipedia.org/wiki/EDTA (6 pages).*
Lloyd-Williams et al., caplus an 1997:43089 (1 page).*
Hu et al., "Synthesis and structure-activity relationship of n-alikyl gly-boro-pro inhibitors of dpp4, fap and dpp7", Bioorg. Med Chem Lett, 15, 2005, 4239-4242.*
Tran et al., "Synthesis and structure-activity relationship of n-acyl-gly-n-acyl-sar and n-blocked-boropro inhibitors of fap, dpp4, and pop", Bioorg. & Med Chem Lett, 17, 2007, 1438-1442.*
Megard et al., "A co-culture based model of human blood-brain barrier: application to active transport of indinavir and in vivo-in vitro correlation", Brain Research, 927, 2002, 153-167.*

(Continued)

*Primary Examiner*—Kamal Saeed
*Assistant Examiner*—Sun Jae Y Loewe
(74) *Attorney, Agent, or Firm*—Alex Andrus; I. Shannon Chi

(57) ABSTRACT

Amino terminus-blocked peptide boronate compounds of Formulas I and II are useful for inhibiting Fibroblast Activation Protein (FAP) and other proteases, and for treating disorders mediated by FAP. Methods of using the amino terminus blocked peptide boronate compounds, and stereoisomers, tautomers, solvates and pharmaceutically acceptable salts thereof, for in vitro, in situ, and in vivo diagnosis, prevention or treatment of such disorders in mammalian cells, or associated pathological conditions are disclosed.

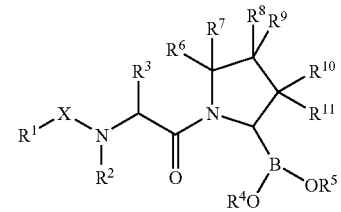

I

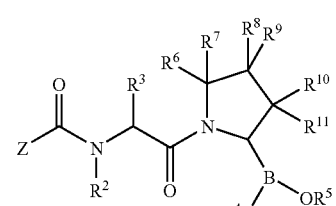

II wherein Z is

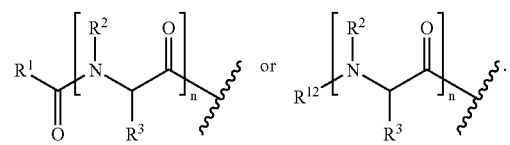

21 Claims, 17 Drawing Sheets

OTHER PUBLICATIONS

Cheng et al., "Promotion of tumor growth by murine fibroblast activation protein, a serine protease, in an animal model", Cancer Research, 62, 4767-4772.*

Edosada et al, "Selective inhibition of fibroblast activation protein protease based on dipeptide substrate specificty", The Journal of Biol. Chem, 2006, 281, 7437-7444.*

Venalailen et al., "Binding kinetics and duration of in vivo action of novel prolyl oligopedtidase inhibitors", Biochem. Pharm, 71, 2006, 683-692.*

Zips et al, "new anticancer agents: in vitro and in vivo", in vivo, 2005, 19, 1-7.* fact sheet Alzheimers association, 2 pages.* http://www.mayoclinic.com/health/alzheimers-disease/DS00161/DSECTION=3, (2 pages).* http://www.medindia.net/patients/patientinfo/Alzheimers_treatment.htm.* http://en.wikipedia.org/wiki/Lanthionine (2 pages).*

Kelly et al., "Immunosuppressive Boronic Acid Dipeptides: Correlation between Conformation and Activity" *J. Am. Chem. Soc.* 115:12637-12638 (1993).

Adams et al., "PT-100, a Small Molecule Dipeptidyl Peptidase Inhibitor, Has Potent Antitumor Effects and Augments Antibody-Mediated Cytotoxicity via a Novel Immune Mechanism" *Cancer Research* 64:5471-5480 (Aug. 1, 2004).

Aertgeerts et al., "Structural and kinetic analysis of the substrate specificity of human fibroblast activation protein alpha" *Journal of Biological Chemistry* 280(20):19441-19444 (May 20, 2005).

Bachovchin et al., "Inhibition of IgA1 proteinases from *Neisseria gonorrhoeae* and *Hemophilus influenzae* by peptide prolyl boronic acids" *J Biol Chem.* 267(7):3738-3743 (Mar. 5, 1990).

Cheng et al., "Abrogation of fibroblast activation protein enzymatic activity attenuates tumor growth" *Mol Cancer Ther.* 4:351-360 (2005).

Coutts et al., "Structure-activity relationships of boronic acid inhibitors of dipeptidyl peptidase IV. 1. Variation of the P2 position of Xaa-boroPro dipeptides" *J Med Chem.* 39(10):2087-2094 (May 10, 1996).

Coutts et al., "Two efficient Methods For The Cleavage Of Pinanediol Boronate Esters Yielding The Free Boronic Acids" *Tetrahedron Letters* 35(29):5109-5112 (1994).

Edosada et al., "Selective inhibition of fibroblast activation protein protease based on dipeptide substrate specificity" *J Biol Chem.* 281(11):7437-7444 (Mar. 17, 2006).

Flentke et al., "Inhibition of dipeptidyl aminopeptidase IV (DP-IV) by Xaa-boroPro dipeptides and use of these inhibitors to examine the role of DP-IV in T-cell function" *Proc Natl Acad Sci U S A.* 88(4):1556-1559 (Feb. 15, 1991).

Gao et al., "Direct Selection for Catalysis from Combinatorial Antibody Libraries Using a Boronic Acid Probe: Primary Amide Bond Hydrolysis" *J. Am. Chem. Soc.* 120(10):2211-2217 (Mar. 18, 1998).

Gibson et al., "A Practical Synthesis of L-Valyl-pyrrolidine-(2R)-boronic Acid: Efficient Recycling of the Costly Chiral Auxiliary (+)-Pinanediol" *Organic Process Research & Development* 6:814-816 (2002).

Hu et al., "Synthesis and structure-activity relationship of N-alkyl Gly-boro-Pro inhibitors of DPP4, FAP, and DPP7" *Bioorg Med Chem Lett.* 15(19):4239-4242 (Oct. 1, 2005).

Jones et al., "Hematopoietic stimulation by a dipeptidyl peptidase inhibitor reveals a novel regulatory mechanism and therapeutic treatment for blood cell deficiencies" *Blood* 102(5):1641-1648 (Sep. 1, 2003).

Kelly et al., "The Efficient Synthesis and Simple Resolution of a Prolineboronate Ester Suitable for Enzyme-Inhibition Studies" *Tetrahedron Letters* 49(5):1009-1016 (1993).

Rosenblum et al., "Prolyl peptidases: a serine protease subfamily with high potential for drug discovery" *Curr Opin Chem Biol.* 7(4):496-504 (Aug. 2003).

Shreder et al., "Boro-norleucine as a P1 residue for the design of selective and potent DPP7 inhibitors" *Bioorg Med Chem Lett.* 15(19):4256-4260 (Oct. 1, 2005).

Snow et al., "Studies on Proline Boronic Acid Dipeptide Inhibitors of Dipeptidyl Peptidase IV: Indentification of a Cyclic Species Containing a B-N Bond" *J. Am. Chem. Soc.* 116:10860-10869 (1994).

Venalainen et al., "Binding kinetics and duration of in vivo action of novel prolyl oligopeptidase inhibitors" *Biochem Pharmacol.* 71(5):683-692 (Feb. 28, 2006).

* cited by examiner

■ Gly-Pro-AFC
△ Ac-Gly-Pro-AFC

FIBROBLAST ACTIVATION PROTEIN INHIBITOR COMPOUNDS AND METHODS

This non-provisional application filed under 37 CFR § 1.53(b) claims the benefit under 35 USC § 119(e) of U.S. Provisional Application Ser. No. 60/682,970 filed on 19 May 2005, and U.S. Provisional Application Ser. No. 60/730,292 filed on 25 Oct. 2005, both of which are incorporated by reference in their entirety.

FIELD OF THE INVENTION

The invention relates to N-blocked peptide proline boronate compounds which are inhibitors of prolyl peptidases including Fibroblast Activation Protein (FAP), as well as compositions containing these compounds and methods of use. The N-blocked peptide proline boronate compounds are useful for inhibiting FAP and for treating disorders mediated thereby. The invention also relates to methods of using N-acylated dipeptide proline boronate compounds for in vitro, in situ, and in vivo diagnosis or treatment of mammalian cells, or associated pathological conditions.

BACKGROUND OF THE INVENTION

After the initial tumorigenic events triggered by genetic mutations of oncogenes and tumor suppressor genes occurring within tumor cells, tumor-host interactions remain as an intrinsic property for each of the critical steps leading to cancer disease progression. Growth and metastasis of solid neoplasms require the recruitment of a supporting tumor stroma, the connective tissue framework. The stromal compartment of a tumor comprises a variety of host cells, including endothelial cells, fibroblasts, and inflammatory cells. It is becoming increasingly appreciated that these host-derived cells infiltrate into tumor tissue, interact with tumor cells, and are subsequently conscripted by tumor cells to produce an array of soluble and insoluble factors that stimulate tumor angiogenesis, growth, and metastasis. These factors include integrins and cell adhesion molecules, extracellular matrix metalloproteinase inducer, as well as fibroblast activation protein (FAP, also known as seprase) that mediate the crosstalking between tumor cells and "hijacked" host stromal cells (Yan et al (2004) Preclinica 2(6):422-426). A highly consistent trait of tumor stromal fibroblasts in most epithelial cancers is the induction of FAP, a member of the serine protease family. Tumor-associated stromal cells can promote epithelial tumorigenesis, suggesting that stromal proteins may represent novel therapeutic targets (Bhowmick et al (2005) Current Opinion in. Genetics and Development 15:97-101; Joyce, J. A. (2005) Cancer Cell 7:513-520).

FAP is a cell surface serine protease expressed at sites of tissue remodeling in embryonic development. FAP is not expressed by mature somatic tissues except activated melanocytes and fibroblasts in wound healing or tumor stroma. FAP expression is specifically silenced in proliferating melanocytic cells during malignant transformation (Ramirez-Montagut et al (2004) Oncogene 23(32):5435-5446). FAP belongs to the prolyl peptidase family, which comprises serine proteases that cleave peptide substrates after a proline residue (Rosenblum et al (2003) Current Opinion in Chemical Biology 7(4):496-504; Sedo et al (2001) Biochimica et biophysica acta 1550(2):107-116; Busek et al (2004) Intl. Jour. of Biochem. & Cell Biol. 36:408-421). The prolyl peptidase family also includes dipeptidyl peptidase IV (DPP IV; also termed CD26), DPP7 (DPP II; quiescent cell proline dipeptidase), DPP8, DPP9, and prolyl carboxypeptidase (PCP; angiotensinase C). More distant members include prolyl oligopeptidase (POP or prolyl endopeptidase (PEP); post-proline cleaving enzyme; Ito, K. et al (2004) Editor(s): Barrett, Rawlings, Woessner, Handbook of Proteolytic Enzymes (2nd Edition) 2:1897-1900, Elsevier, London, UK; Polgar, L. (2002) Cellular and Molecular Life Sciences 59, 349-362) and acylaminoacylpeptidase (AAP; acylpeptide hydrolase (APH)). Proline peptidases and related proteins contain both membrane-bound and soluble members and span a broad range of expression patterns, tissue distributions and compartmentalization. These proteins have important roles in regulation of signaling by peptide hormones, and are emerging targets for diabetes, oncology, and other indications.

FAP (seprase) was isolated from bovine serum, purified to homogeneity, and sequenced (Collins et al (2004) Intl. Jour. of Biochem. & Cell Biol. 36(11):2320-2333). The protease activity of bovine FAP in cleaving synthetic peptide substrates suggests that: (i) multiple subsites in FAP are involved in enzyme-substrate binding, with the smallest peptide cleaved being a tetrapeptide; (ii) there is high primary substrate specificity for the Pro-X bond; and (iii) there is a preference for a hydrophobic residue at the C-terminal end of the scissile bond.

It was demonstrated that FAP has both dipeptidyl peptidase and collagenolytic activity capable of degrading gelatin and type I collagen. The expression and enzyme activity of FAP in benign and malignant melanocytic skin tumors has been established, indicating a possible role for FAP in the control of tumor cell growth and proliferation during melanoma carcinogenesis (Huber et al (2003) Jour. of Investigative Dermatology 120(2):182-188), colorectal cancer (Satoshi et al (2003) Cancer letters 199(1):91-98), and breast cancer (Goodman et al (2003) Clinical & Exp. Metastasis 20(5):459-470), as well as all of breast, colon, and lung cancer (Park et al (1999) J. Biol. Chem. 274:36505-36512). Furthermore, FAP seems to upregulated in cirrhosis (Levi, M T et al (1999) Hepatology 29:1768-1778), fibromatosis (Skubitz, K M et al J. Clin. Lab. Med. (2004) 143(2):89-98), and rheumatoid arthritis.

The fibroblast activation protein alpha (FAPα) was discovered with a monoclonal antibody, mAb F19, that was generated in the course of a serological survey of cell surface antigens expressed on cultured human fibroblasts, sarcomas and neuroectodermal tumor cells. This antibody was used to characterize the plasma membrane-associated 95 kDa FAPα glycoprotein, to isolate the FAP-encoding cDNA, and to examine FAPα expression in a broad range of normal and neoplastic human tissues (Park, John E.; Rettig, Wolfgang J., Editor(s): Barrett, Alan J.; Rawlings, Neil D.; Woessner, J. Fred, Handbook of Proteolytic Enzymes (2nd Edition) (2004) 2:1913-1917, Publisher: Elsevier, London, UK).

Maturation of blood cells via hematopoiesis involves cytokines and their regulation by the serine proteases CD26/dipeptidyl-peptidase IV (DPP-IV), as well as FAP (McIntyre et al (2004) Drugs of the Future 29(9):882-886; Ajami et al (2003) Biochemistry 42(3):694-701). The human fibroblast activation protein (FAPα) is a $M_f$ 95,000 cell surface molecule originally identified with monoclonal antibody (mAb) F19 (Rettig et al. (1988) Proc. Natl. Acad. Sci. USA 85, 3110-3114; Rettig et al. (1993) Cancer Res. 53, 3327-3335; Rettig et al (1994) Intl. Jour. of Cancer 58(3):385-392). The FAP gene, localized to chromosome 2 in humans (Mathew et al (1995) Genomics 25(1):335-337) is a 2812 nt sequence with an open reading frame of 2277 bp conserved throughout a variety of species including mouse, hamster, and *Xenopus laevis* (Scanlan et al (1994) Proc. Natl. Acad. Sci. USA 91:5657-5661; Park et al (1999) J. Biol. Chem. 274:36505-

36512; Niedermeyer et al (1998) Eur. J. Biochem. 254:650-654). The corresponding FAP protein product contains 759 or 760 amino acids and has a calculated molecular weight of about 88 kDa. The primary amino acid sequence is homologous to type II integral membrane proteins, which are characterized by a carboxy-terminal end that is large and corresponds to the extra-cellular domain (ECD), a hydrophobic transmembrane segment, and a short cytoplasmic tail. FAP is highly homologous to dipeptidyl peptidase IV (DDPIV) in various species, with 61% nucleotide sequence identity and 48% amino acid sequence identity to DPPIV. Although both FAP and DDPIV have peptidase (protease) activity, biochemical and serological studies show that these proteins are significantly different in their enzymatic activity with synthetic substrates as well as their functional activation of T lymphocytes (DDPIV induction) or reactive stromal fibroblasts (FAP induction (Mathew et al (1995) Genomics w5:335-337). The FAPα cDNA codes for a type II integral membrane protein with a large extracellular domain, transmembrane segment, and short cytoplasmic tail (Scanlan et al. (1994) Proc. Natl. Acad. Sci. USA 91, 5657-5661; U.S. Pat. No. 6,846,910; WO 97/34927; U.S. Pat. No. 5,767,242; U.S. Pat. No. 5,587,299; U.S. Pat. No. 5,965,373). FAPα shows 48% amino acid sequence identity to the T-cell activation antigen CD26, also known as dipeptidyl peptidase IV (DP-PIV; EC 3.4.14.5), a membrane-bound protein with dipeptidyl peptidase activity. FAPα has enzymatic activity and is a member of the serine protease family, with serine 624 being critical for enzymatic function WO 97/34927; U.S. Pat. No. 5,965,373). Seprase (FAPα) is a homodimeric 170 kDa integral membrane gelatinase whose expression correlates with the invasiveness of the human melanoma cell line LOX (Pineiro-Sanchez et al (1997) Jour. of Biol. Chem. 272(12): 7595-7601), and which promotes rapid tumor growth in a mouse model of human breast cancer (Huang et al (2004) Cancer Res. 64:2712-2716). Molecular cloning of a cDNA encodes the 97 kDa subunit of seprase with a deduced amino acid sequence that predicts a type II integral membrane protein with a cytoplasmic tail of 6 amino acids, followed by a transmembrane domain of 20 amino acids and an extracellular domain of 734 amino acids. The carboxyl terminus contains a putative catalytic region (approximately 200 amino acids) which is homologous (68% identity) to that of the nonclassical serine protease dipeptidyl peptidase IV (DP-PIV). The conserved serine protease motif G-X-S-X-G is present as G-W-S-Y-G. However, sequence analysis of seprase cDNA from LOX and other cell lines strongly suggests that seprase and human fibroblast activation protein α (FAPα) are products of the same gene and are essentially identical (Goldstein et al (1997) Biochimica et Biophysica Acta 1361(1):11-19).

FAPα is selectively expressed in reactive stromal fibroblasts of many histological types of human epithelial cancers, granulation tissue of healing wounds, and malignant cells of certain bone and soft tissue sarcomas. Normal adult tissues are generally devoid of detectable FAPα (Chen et al (2003) Adv. Exp. Med. Biol. 524:197-203), but some fetal mesenchymal tissues transiently express the molecule. In contrast, most of the common types of epithelial cancers, including >90% of breast, non-small-cell lung, and colorectal carcinomas, contain FAPα-reactive stromal fibroblasts. These FAPα+ fibroblasts accompany newly formed tumor blood vessels, forming a distinct cellular compartment interposed between the tumor capillary endothelium and the basal aspect of malignant epithelial cell clusters (Welt et al. (1994) J. Clin. Oncol. 12(6), 1193-1203). While FAPα+ stromal fibroblasts are found in both primary and metastatic carcinomas, the benign and premalignant epithelial lesions tested, such as fibroadenomas of the breast and colorectal adenomas, only rarely contain FAPα+ stromal cells. Based on the restricted distribution pattern of FAPα in normal tissues and its uniform expression in the supporting stroma of many malignant tumors, clinical trials with $^{131}$I-labelled mAb F19 have been initiated in patients with metastatic colon carcinomas (Tanswell et al (2001) British Jour. of Clin. Pharm. 51(2):177-180). Evidence for the promotion of tumor growth by murine FAP, and inhibition of tumor growth by antibody inhibitors of FAP was demonstrated by Cheng et al (2002) 62:4767-4772. Human FAP was expressed and targetted by $^{131}$I-labelled humanized anti-FAP mAb in a human skin/severe combined immunodeficient mouse breast cancer xenograft model (Tahtis et al (2003) Molecular Cancer Therapeutics 2(8):729-737).

A high-resolution X-ray crystal structure of the extracellular domain of FAPα revealed a difference from DPP-IV in their active sites. Kinetic analysis of an active site mutant of FAPα, A657D, with dipeptide substrates showed an increase in the rate of cleavage for a free amino terminus substrate but a decrease for the corresponding N-benzyloxycarbonyl substrate, relative to wild type FAPα (Aertgeerts et al (2005) J. Biol. Chem., April; 10. 1074/jbc.C500092200).

Four completely human antibody derivatives (single-chain-antibody fragments, scFvs) with specificity for FAP as a general tumor stroma marker were isolated by guided selection. Highly diverse IgG, IgM and IgD isotypes comprising heavy-chain variable domain libraries were generated using cDNAs derived from diverse lymphoid organs of a multitude of donors (Schmidt et al (2001) European Jour. of Biochemistry 268(6):1730-1738). Other recombinant FAP-binding proteins with framework modifications have been expressed (U.S. Pat. No. 6,455,677). Although attempts to fully block FAP activity with antibodies have not been successful (Cheng, et al (2004) Abrogation of Fibroblast Activation Protein Enzymatic Activity Attenuates Tumor Growth. In. American Association for Cancer Research, 95th Annual Meeting, Orlando, Fla.), Sibrotuzumab, a humanized monoclonal antibody directed against FAP, is in human clinical trials for cancer therapy (Kloft et al (2004) Investigational New Drugs 22(1):39-52; Scott et al (2003) Clinical Cancer Research 9(5): 1639-1647; Cheng et al (2003) Clinical Cancer Research 9(5):1590-1595; Hofheinz et al (2003 February) Onkologie 26(1):44-8).

The amino boronic dipeptide (talabostat, PT-100, Val-boro-Pro; Point Therapeutics), a dipeptidyl peptidase (DPP) inhibitor, has been shown to up-regulate gene expression of certain cytokines in hematopoietic tissue via a high-affinity interaction, which appears to involve fibroblast activation protein (US 2003/0158114; US 2004/0152192; Adams et al (2004) Cancer Research 64(15):5471-5480; Jones et al (2003) Blood 102(5):1641-1648). Because FAP is also expressed in stroma of lymphoid tissue and tumors, the effect of PT-100 on tumor growth was studied in mice in vivo although PT-100 has no direct cytotoxic effect on tumor cells in vitro. Oral administration of PT-100 to mice slowed growth of syngeneic tumors derived from fibrosarcoma, lymphoma, melanoma, and mastocytoma cell lines. Treatment of mice with PT-100 resulted in tumor growth attenuation in a tumor model characterized by murine FAP expression in the surrounding tumor stromal fibroblasts (Cheng et al (2005) Mol. Cancer Ther. 4(3):351-60). However, PT-100 is not FAP-specific because it also inhibits DPP-8 and DPP-9. In addition, PT-100 demonstrates a self-inactivation mechanism by intramolecular cyclization of the N-terminus amine and the boronate group. A phase I/II human clinical study has been initiated to test the safety and efficacy of talabostat in combination with RITUXAN® (Genentech, Inc.) in patients with hematologic malignancies, such as non-Hodgkin's lymphoma and chronic lymphocytic leukemia. Other inhibitors targeting prolyl peptidases, include: Val-BoroPro compounds (Flentke et al (1991) Proc. Natl. Acad. Sci. USA 88:1556-1559; Coutts et al (1996) J. Med. Chem. 39:2087-2094; Shreder et al. (2005) Bioorganic and Medicinal Chemistry Letters 15:4256-4260); N-acyl-Gly-BoroPro compounds (Edosada et al (2006) Jour. Biological Chem. 281(11):7437-7444); N-alkyl-Gly-BoroPro compounds (Hu, et al (2005) Bioorganic and Medicinal Chemistry Letters 15:4239-4242); 1-(2'-aminoacyl)-2-cyanopyrrolidine compounds (WO 2001/040180); and Boro-norleucine compounds (Shreder et al (2005) Bioorganic and Medicinal Chemistry Letters 15:4256-4260).

Peptidic prodrugs which are FAP cleavage substrates have been reported to be converted to cytotoxic or cytostatic metabolites by the sequence selective cleavage of FAP (U.S. Pat. No. 6,613,879; US 2003/021979; US 2003/0232742; US 2003/0055052; US 2002/0155565). Peptide proline-boronate protease inhibitors have been reported (Bachovchin et al (1990) Jour. Biol. Chem. 265(7):3738-3743; Flentke et al (1991) Proc. Natl. Acad. Sci. 88:1556-1559; Snow et al (1994) J. Amer. Chem. Soc. 116(24):10860-10869; Coutts et al (1996) J. Med. Chem. 39:2087-2094; U.S. Pat. No. 4,935,493; U.S. Pat. No. 5,288,707; U.S. Pat. No. 5,462,928; U.S. Pat. No. 6,825,169; WO 2003/092605; US 2004/0229820; WO 2005/047297). Cyclic boro-proline compounds are reported to be useful for oral administration (U.S. Pat. No. 6,355,614). An N-acetyl lysine proline boronate compound has been proposed as an antibacterial agent (U.S. Pat. No. 5,574,017).

SUMMARY

The compounds of the invention include N-blocked dipeptide proline boronate (Formula I) compounds and N-blocked peptide proline boronate (Formula II) compounds. Formula I and II compounds can be used in the treatment of hyperproliferative disorders, such as cancer.

In one aspect, the compounds of the invention having Formulas I and II are inhibitors of fibroblast activation protein (FAP).

In another aspect, the compounds of the invention having Formulas I and II are inhibitors of prolyl oligopeptidase (POP).

Another aspect of the invention is to provide methods of inhibiting FAP activity by contacting the enzyme with an effective inhibitory amount of Formulas I and II compounds, or a composition containing these compounds.

Another aspect of the invention are methods of preventing or treating: a hyperproliferative disorder such as cancer, neurodegeneration, cardiac hypertrophy, pain, migraine, neurotraumatic disease, cirrhosis, fibromatosis, and rheumatoid arthritis by administering to a mammal in need of such treatment an effective amount of one of the compounds of the invention, or a composition containing the compound and a carrier or excipient.

Another aspect of the invention are methods of preventing or treating cancer by administering to a mammal in need of such treatment an effective amount of one of the compounds of the invention in combination with one or more additional compounds with anti-cancer properties.

Another aspect of the invention is the use of a compound of Formula I or II in the manufacture of medicament for the treatment of a hyperproliferative disorder.

Another aspect of the invention includes imaging probes for localization and detection of FAP or other prolyl peptidase activity. Imaging probes comprise a compound of Formula I or II conjugated to an imaging or contrast agent.

Another aspect of the invention includes articles of manufacture, i.e. kits, comprising a proline boronate compound of Formula I or II in a container, and a package insert or label indicating a treatment.

Another aspect of the invention includes methods of preparing, methods of synthesis, methods of separation, and methods of purification of the proline boronate compounds of Formulas I and II.

The invention may be understood by reference to the following detailed description of the exemplary embodiments, taken in conjunction with the accompanying drawings, figures, and Examples. The discussion below is descriptive, illustrative and exemplary and is not to be taken as limiting the scope defined by any appended claims.

DETAILED DESCRIPTION OF EXEMPLARY EMBODIMENTS

Figure 1:
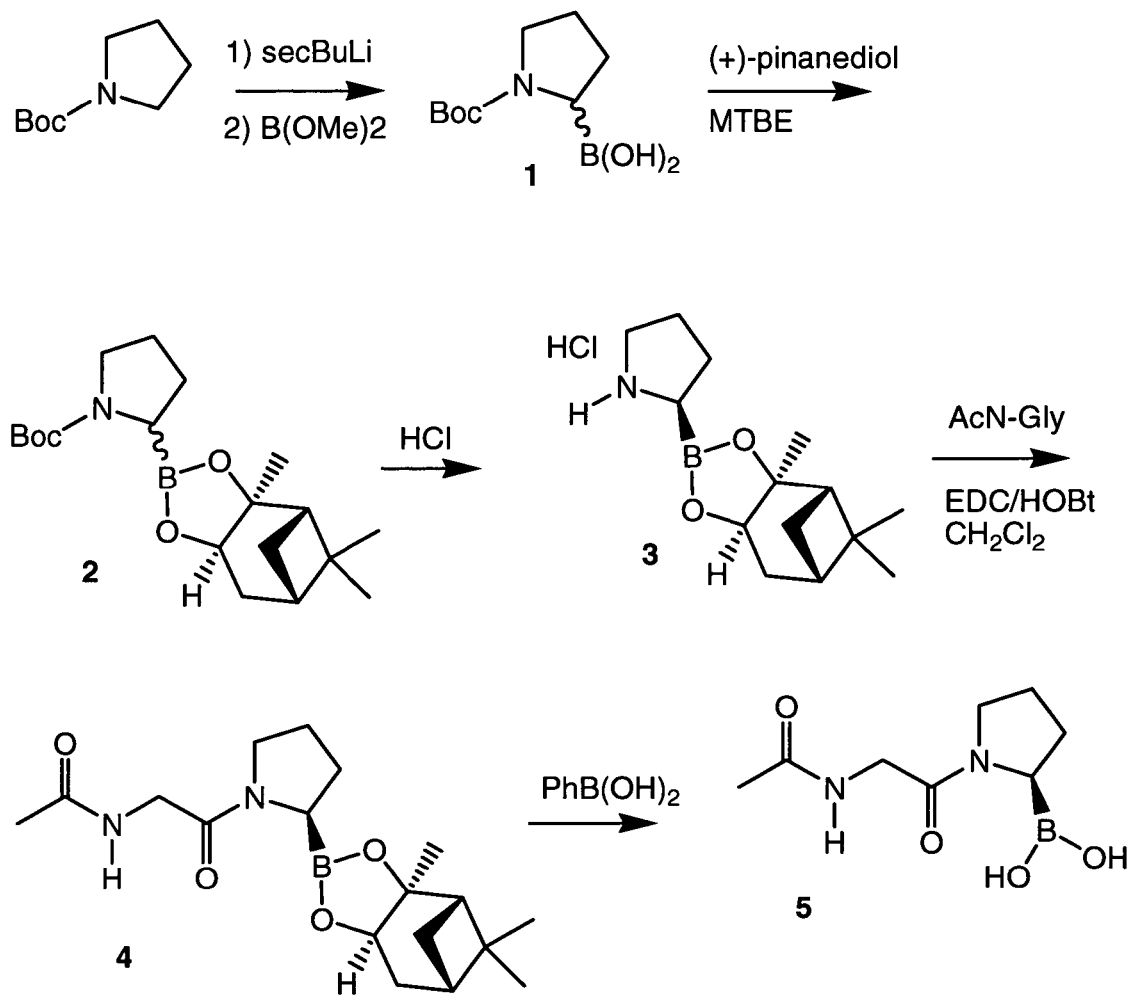
FIG. 1 shows an exemplary synthetic route to N-acetyl-gly-boroproline 5 from tert-butyl 1-pyrrolidinecarboxylate.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

Definitions

Unless stated otherwise, the following terms and phrases as used herein are intended to have the following meanings:

"Alkyl" is an acyclic $C_1$-$C_{18}$ hydrocarbon moiety containing normal, secondary, tertiary or spirocyclic carbon atoms. Examples of alkyl radicals include $C_1$-$C_8$ hydrocarbon moieties such as: methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 1-heptyl, 1-octyl.

"Alkenyl" is an acyclic $C_2$-$C_{18}$ hydrocarbon moiety containing normal, secondary, tertiary or cyclic carbon atoms with at least one site of unsaturation, i.e. a carbon-carbon, sp$^2$ double bond. Examples include, but are not limited to: ethylene or vinyl (—CH=CH$_2$), allyl (—CH$_2$CH=CH$_2$), isobutenyl, 5-hexenyl (—CH$_2$CH$_2$CH$_2$CH$_2$CH=CH$_2$).

"Alkynyl" is an acyclic $C_2$-$C_{18}$ hydrocarbon moiety containing normal, secondary, tertiary or cyclic carbon atoms with at least one site of unsaturation, i.e. a carbon-carbon, sp triple bond. Examples include, but are not limited to: acetylenic (—C≡CH) and propargyl (—CH$_2$C≡CH), "Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—CH$_2$—) 1,2-ethyl (—CH$_2$CH$_2$—), 1,3-propyl (—CH$_2$CH$_2$CH$_2$—), 1,4-butyl (—CH$_2$CH$_2$CH$_2$CH$_2$—), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH=CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to: acetylene (—C≡C—), propargyl (—CH$_2$C≡C—), and 4-pentynyl (—CH$_2$CH$_2$CH$_2$C≡C—).

"Carbocycle" and "carbocyclyl" mean a non-aromatic, saturated or unsaturated ring having 3 to 12 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system, or as bridged systems such as bicyclo[2.2.1]heptane, bicyclo [2.2.2]octane, and bicyclo[3.2.2]nonane. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl.

"Aryl" means a monovalent aromatic hydrocarbon radical of 6-20 carbon atoms derived by the removal of one hydrogen atom from a single carbon atom of a parent aromatic ring system. Some aryl groups are represented in the exemplary structures as "Ar". Aryl includes a bicyclic radical comprising an aromatic ring with a fused non-aromatic or partially saturated ring. Typical aryl groups include, but are not limited to, radicals derived from benzene, substituted benzene, naphthalene, anthracene, biphenyl, indenyl, indanyl, 1,2-dihydronapthalene, 1,2,3,4-tetrahydronapthyl, and the like.

"Heteroaryl", "heterocyclyl", and "heterocycle" all refer to a ring system in which one or more ring atoms is a heteroatom, e.g. nitrogen, oxygen, and sulfur. The heterocyclyl radical comprises 1 to 20 carbon atoms and 1 to 6 heteroatoms selected from N, O, P, and S. The heterocyclyl radical may saturated or unsaturated. The heterocyclyl radical may be aromatic or not aromatic. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566.

Examples of heterocyclyl radicals include by way of example and not limitation, pyridyl, dihydroypyridyl, 4-dialkylaminopyridinium, tetrahydropyridyl (piperidyl), thiazolyl, tetrahydrothiophenyl, sulfur-oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, 3-oxo-tetrahydrofuranyl, 3-oximinio-tetrahydrofuranyl, bis-tetrahydrofuranyl, tetrahydropyranyl, 4-oxo-tetrahydropyranyl, 4-oximino-tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

Substituents may also be combinations of alkylene, alkenylene, alkynylene, carbocycle, aryl, and heteroaryl radicals, such as cyclopropylmethyl, cyclohexylethyl, benzyl, and N-ethylmorpholino, and substituted forms thereof.

"Substituted alkyl", "substituted aryl", "substituted heterocyclyl", and "substituted carbocyclyl" mean alkyl, aryl, heterocyclyl and carbocyclyl respectively, in which one or more hydrogen atoms are each independently replaced with a substituent. Typical substituents include, but are not limited to, F, Cl, Br, I, OH, OR, R, =O, =S, =NR, =N$^+$(O)(R), =N(OR), =N$^+$(O)(OR), =N—NR$_2$, —C(=Y)R, —C(=Y)OR, —C(=Y)NR$_2$, —NR$_2$, —N$^+$(R)$_3$, —N(R)C (=Y)R, —N(R)C(=Y)OR, —N(R)C(=Y)NR$_2$, —SR, —OC(=Y)R, —OC(=Y)OR, —OC(=Y)NR$_2$, —OS(O)$_2$ (OR), —OP(=Y)(OR)$_2$, —OP(OR)$_2$, —P(=Y)(OR)$_2$, —P(=Y)(OR)NR$_2$, —S(O)R, —S(O)$_2$R, —S(O)$_2$NR, —S(O)(OR), —S(O)$_2$(OR), —SC(=Y)R, —SC(=Y)OR, =Y, and —SC(=Y)NR$_2$; where each R is H, C$_1$-C$_8$ alkyl, C$_1$-C$_8$ alkenyl, C$_1$-C$_8$ alkynyl, C$_6$-C$_{20}$ aryl, C$_2$-C$_{20}$ heterocycle, or a protecting group; and Y is independently O, S, NR, $^+$N(O)(R), N(OR), $^+$N(O)(OR), or N—NR$_2$. Alkylene, alkenylene, and alkynylene groups as described above may also be similarly substituted.

The term "amino acid side chain" includes those groups found in: (i) naturally occurring amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine; (ii) minor amino acids such as ornithine and citrulline; (iii) synthetic analogs and derivatives of naturally occurring amino acids; and (iv) all enantiomers, diastereomers, isomerically enriched, isotopically labelled, protected forms, and racemic mixtures thereof.

The terms "treat" or "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR).

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

The term "prodrug" as used in this application refers to a precursor or derivative form of a pharmaceutically active substance that is less cytotoxic to tumor cells compared to the parent drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

A "liposome" is a small vesicle composed of various types of lipids, phospholipids and/or surfactant which is useful for delivery of a drug (such as the N-acylated dipeptide proline boronate inhibitors disclosed herein and, optionally, a chemotherapeutic agent) to a mammal. The components of the liposome are commonly arranged in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. Many organic compounds exist in optically active forms, i.e., they have the ability to rotate the plane of plane-polarized light. In describing an optically active compound, the prefixes D (d) and L (1), or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture"

and "racemate" refer to an equimolar mixture of two enantiomeric species, devoid of optical activity.

The phrase "pharmaceutically acceptable salt," as used herein, refers to pharmaceutically acceptable organic or inorganic salts of a compound of the invention. Exemplary salts include, but are not limited, to sulfate, citrate, acetate, trifluoroacetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" or "Pg" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —CH$_2$CH$_2$SO$_2$Ph, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The term "animal" refers to humans (male or female), companion animals (e.g., dogs, cats and horses), food-source animals, zoo animals, marine animals, birds and other similar animal species. "Edible animals" refers to food-source animals such as cows, pigs, sheep and poultry.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment.

The term "boroPro" refers to the substructural analog of proline in which the carboxylate group [COOH] at the 2-position of the pyrrolidinyl ring is replaced with a boronyl group [B(OR$^4$)(OR$^5$)], and having the substructure:

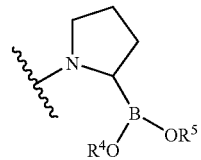

where the wavy line indicates the site of attachment to the carbonyl group forming an amide in Formula I and II compounds.

Amino Terminus-Blocked Peptide Proline Boronate Compounds

Amino terminus-blocked peptide proline boronate compounds of Formulas I and II are useful for inhibiting Fibroblast Activation Protein (FAP) and other proteases, and for treating disorders mediated by FAP.

The present invention provides N-blocked dipeptide proline boronate compounds having Formula I, and pharmaceutical compositions and formulations thereof, that are potentially useful in the treatment of diseases, conditions and/or disorders modulated by Fibroblast Activation Protein (FAP) or other proteases. Formula I compounds include:

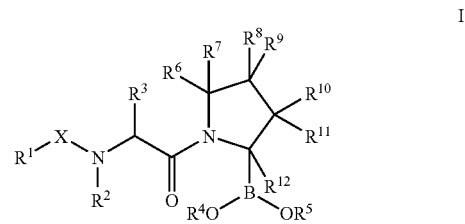

and stereoisomers, tautomers, solvates and pharmaceutically acceptable salts thereof, wherein:

X is C(=O), C(=NR), NRC(=O), NRC(=NR), OC(=O), OC(=NR), P(O)(OR), S(O), and S(O)$_2$;

R$^1$ is selected from H, C$_1$-C$_8$ alkyl, C$_2$-C$_8$ alkenyl, C$_2$-C$_8$ alkynyl, C$_2$-C$_{20}$ heterocycle, C$_3$-C$_{12}$ carbocycle, and C$_6$-C$_{20}$ aryl;

R$^2$ is selected from H, C$_1$-C$_8$ alkyl, C$_2$-C$_8$ alkenyl, C$_2$-C$_8$ alkynyl, C$_2$-C$_{20}$ heterocycle, C$_3$-C$_{12}$ carbocycle, and C$_6$-C$_{20}$ aryl;

or R$^1$ and R$^2$ form a C$_2$-C$_{20}$ heterocycle;

R$^3$ is an optionally protected amino acid side chain;

R$^4$ and R$^5$ are independently selected from H, C$_1$-C$_8$ alkyl, C$_2$-C$_8$ alkenyl, C$_2$-C$_8$ alkynyl, C$_2$-C$_{20}$ heterocycle, C$_3$-C$_{12}$ carbocycle, C$_6$-C$_{20}$ aryl, a prodrug, and a protecting group; or R$^4$ and R$^5$ together form a C$_6$-C$_{20}$ aryl, a C$_3$-C$_{12}$ carbocycle, a prodrug, or a protecting group;

R$^6$, R$^7$, R$^8$, R$^9$, R$^{10}$, R$^{11}$ and R$^{12}$ are independently selected from H, F, Cl, Br, I, OH, OR, R, —C(=Y)R, —C(=Y)OR, —C(=Y)N(R)$_2$, —N(R)$_2$, —N$^+$(R)$_3$, —N(R)C(=Y)R, —N(R)C(=Y)OR, —N(R)C(=Y)N(R)$_2$, —SR, —OC(=Y)R, —OC(=Y)OR, —OC(=Y)(N(R)$_2$), —OS(O)$_2$(OR), —OP(=Y)(OR)$_2$, —OP(OR)$_2$, —P(=Y)(OR)$_2$, —P(=Y)(OR)NR$_2$, —S(O)R, —S(O)$_2$R, —S(O)$_2$NR, —S(O)(OR), —S(O)$_2$(OR), —SC(=Y)R, —SC(=Y)OR, and —SC(=Y)NR$_2$;

each alkyl, alkenyl, alkynyl, aryl, carbocycle, and heterocycle is optionally and independently substituted with one or more substituents selected from F, Cl, Br, I, OH, OR, R, =O, =S, =NR, =N$^+$(O)(R), =N(OR), =N$^+$(O)(OR), =N—N $(R)_2$, —C(=Y)R, —C(=Y)OR, —C(=Y)N(R)$_2$, —N(R)$_2$, —N$^+$(R)$_3$, —N(R)C(=Y)R, —N(R)C(=Y)OR, —N(R)C(=Y)N(R)$_2$, —SR, —OC(=Y)R, —OC(=Y)OR, —OC(=Y)(N(R)$_2$), —OS(O)$_2$(OR), —OP(=Y)(OR)$_2$, —OP(OR)$_2$, —P(=Y)(OR)$_2$, —P(=Y)(OR)NR$_2$, —S(O)R, —S(O)$_2$R, —S(O)$_2$NR, —S(O)(OR), —S(O)$_2$(OR), —SC(=Y)R, —SC(=Y)OR, and —SC(=Y)NR$_2$;

R is H, $C_1$-$C_8$ alkyl, $C_2$-$C_8$ alkenyl, $C_2$-$C_8$ alkynyl, $C_6$-$C_{20}$ aryl, $C_1$-$C_{20}$ heterocyclyl, or a protecting group; and Y is independently O, S, NR, N$^+$(O)(R), N(OR), N$^+$(O)(OR), or N—N(R)$_2$;

with the proviso that when $R^1$ is methyl and X is C(=O), then $R^3$ is not lysine or acetyl-lysine; and that when $R^1$ is tert-butyl and X is OC(=O), then $R^3$ is not methyl.

The present invention also provides N-blocked peptide proline boronate compounds having Formula II, and pharmaceutical compositions and formulations thereof, that are potentially useful in the treatment of diseases, conditions and/or disorders modulated by Fibroblast Activation Protein (FAP) or other proteases. Formula II compounds include:

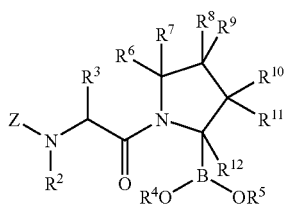

II and stereoisomers, tautomers, solvates and pharmaceutically acceptable salts thereof, wherein:

Z is

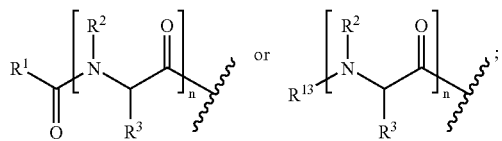

$R^1$ is selected from H, $C_1$-$C_8$ alkyl, $C_2$-$C_8$ alkenyl, $C_2$-$C_8$ alkynyl, $C_2$-$C_{20}$ heterocycle, $C_3$-$C_{12}$ carbocycle, and $C_6$-$C_{20}$ aryl;

$R^2$ is selected from H, $C_1$-$C_8$ alkyl, $C_2$-$C_8$ alkenyl, $C_2$-$C_8$ alkynyl, $C_2$-$C_{20}$ heterocycle, $C_3$-$C_{12}$ carbocycle, and $C_6$-$C_{20}$ aryl;

or $R^1$ and $R^2$ form a $C_2$-$C_{20}$ heterocycle;

$R^3$ is an optionally protected amino acid side chain;

$R^4$ and $R^5$ are independently selected from H, $C_1$-$C_8$ alkyl, $C_2$-$C_8$ alkenyl, $C_2$-$C_8$ alkynyl, $C_2$-$C_{20}$ heterocycle, $C_3$-$C_{12}$ carbocycle, $C_6$-$C_{20}$ aryl, a prodrug, and a protecting group; or $R^4$ and $R^5$ together form a $C_6$-$C_{20}$ aryl, a $C_3$-$C_{12}$ carbocycle, a prodrug, or a protecting group;

$R^6$, $R^7$, $R^8$, $R^9$, $R^{10}$, $R^{11}$ and $R^{12}$ are independently selected from H, F, Cl, Br, I, OH, OR, R, —C(=Y)R, —C(=Y)OR, —C(=Y)N(R)$_2$, —N(R)$_2$, —N$^+$(R)$_3$, —N(R)C(=Y)R, —N(R)C(=Y)OR, —N(R)C(=Y)N(R)$_2$, —SR, —OC(=Y)R, —OC(=Y)OR, —OC(=Y)(N(R)$_2$), —OS(O)$_2$(OR), —OP(=Y)(OR)$_2$, —OP(OR)$_2$, —P(=Y)(OR)$_2$, —P(=Y)(OR)NR$_2$, —S(O)R, —S(O)$_2$R, —S(O)$_2$NR, —S(O)(OR), —S(O)$_2$(OR), —SC(=Y)R, —SC(=Y)OR, and —SC(=Y)NR$_2$;

$R^{13}$ is independently selected from $C_1$-$C_8$ alkyl, $C_2$-$C_8$ alkenyl, $C_2$-$C_8$ alkynyl, $C_6$-$C_{20}$ aryl, $C_1$-$C_{20}$ heterocyclyl, or a protecting group;

each alkyl, alkenyl, alkynyl, aryl, carbocycle, and heterocycle is optionally and independently substituted with one or more substituents selected from F, Cl, Br, I, OH, OR, R, =O, =S, =NR, =N$^+$(O)(R), =N(OR), =N$^+$(O)(OR), =N—N(R)$_2$, —C(=Y)R, —C(=Y)OR, —C(=Y)N(R)$_2$, —N(R)$_2$, —N$^+$(R)$_3$, —N(R)C(=Y)R, —N(R)C(=Y)OR, —N(R)C(=Y)N(R)$_2$, —SR, —OC(=Y)R, —OC(=Y)OR, —OC(=Y)(N(R)$_2$), —OS(O)$_2$(OR), —OP(=Y)(OR)$_2$, —OP(OR)$_2$, —P(=Y)(OR)$_2$, —P(=Y)(OR)NR$_2$, —S(O)R, —S(O)$_2$R, —S(O)$_2$NR, —S(O)(OR), —S(O)$_2$(OR), —SC(=Y)R, —SC(=Y)OR, and —SC(=Y)NR$_2$;

R is H, $C_1$-$C_8$ alkyl, $C_2$-$C_8$ alkenyl, $C_2$-$C_8$ alkynyl, $C_6$-$C_{20}$ aryl, $C_1$-$C_{20}$ heterocyclyl, or a protecting group;

Y is independently O, S, NR, N$^+$(O)(R), N(OR), N$^+$(O)(OR), or N—N(R)$_2$; and n is 1, 2, 3, 4, 5, 6, 7, or 8.

For Formula I and II compounds, R may be a protecting group selected from a trialkylsilyl, a dialkylphenylsilyl, benzoate, benzyl, benzyloxymethyl, methyl, methoxymethyl, a triarylmethyl, phthalimido and tetrahydropyranyl.

For Formula I and II compounds, $R^1$ may be phenyl optionally substituted with one or more substituents selected from F, Cl, Br, I, OH, OR, R, —C(=Y)R, —C(=Y)OR, —C(=Y)NR$_2$, —NR$_2$, —N$^+$(R)$_3$, —N(R)C(=Y)R, —N(R)C(=Y)OR, —N(R)C(=Y)NR$_2$, —SR, —OC(=Y)R, —OC(=Y)OR, —OC(=Y)NR$_2$, —OS(O)$_2$(OR), —OP(=Y)(OR)$_2$, —OP(OR)$_2$, —P(=Y)(OR)$_2$, —P(=Y)(OR)NR$_2$, —S(O)R, —S(O)$_2$R, —S(O)$_2$NR, —S(O)(OR), —S(O)$_2$(OR), —SC(=Y)R, —SC(=Y)OR, and —SC(=Y)NR$_2$.

For Formula I and II compounds, $R^1$ may also be heterocyclyl selected from 2-pyridyl, 3-pyridyl, 4-pyridyl, 2-imidazolyl, 4-imidazolyl, 3-pyrazolyl, 4-pyrazolyl, 2-pyrrolyl, 3-pyrrolyl, 2-thiazolyl, 4-thiazolyl, 5-thiazolyl, 3-pyridazinyl, 4-pyridazinyl, 5-pyridazinyl, 2-pyrimidinyl, 5-pyrimidinyl, 6-pyrimidinyl, 2-pyrazinyl, 2-oxazolyl, 4-oxazolyl, 5-oxazolyl, and substituted forms thereof.

For Formula I and II compounds, $R^3$ is an amino acid side chain including those occurring naturally, as well as minor amino acids and non-naturally occurring amino acid analogs, such as citrulline. $R^3$ includes hydrogen, methyl, isopropyl, isobutyl, sec-butyl, benzyl, p-hydroxybenzyl, —CH$_2$OH, —CH(OH)CH$_3$, —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$, 2-pyridylmethyl-, 3-pyridylmethyl-, 4-pyridylmethyl-, phenyl, cyclohexyl, as well as the following structures:

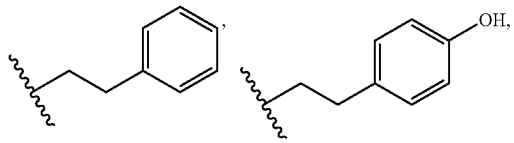

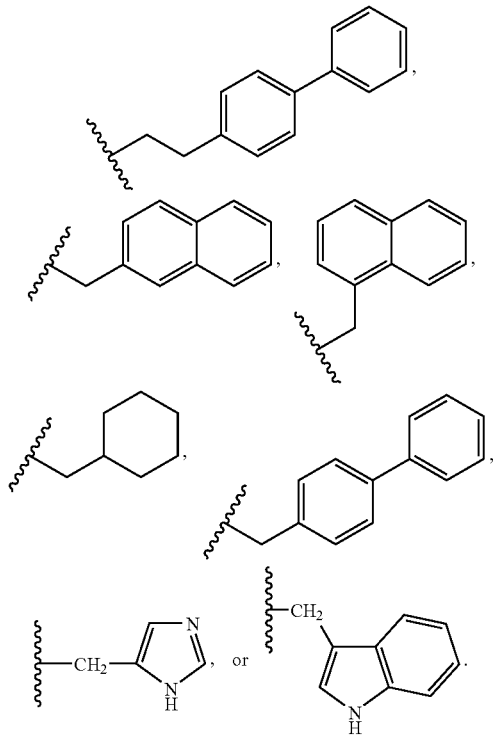

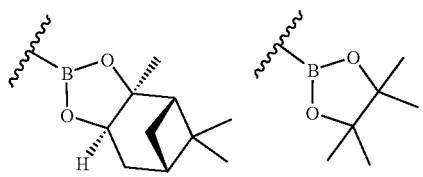

When $R^3$ is other than hydrogen, the carbon atom to which $R^3$ is attached is chiral. Each carbon atom to which $R^3$ is attached is independently in the (S) or (R) configuration, or a racemic mixture. Formula I compounds may thus be enantiomerically pure, racemic, or diastereomeric.

In exemplary embodiments, amino acid side chains $R^3$ are selected from those of natural and non-natural amino acids, including alanine, 2-amino-2-cyclohexylacetic acid, 2-amino-2-phenylacetic acid, arginine, asparagine, aspartic acid, cysteine, glutamine, glutamic acid, glycine, histidine, isoleucine, leucine, lysine, methionine, norleucine, phenylalanine, proline, serine, threonine, tryptophan, tyrosine, valine, γ-aminobutyric acid, α,α-dimethyl γ-aminobutyric acid, β,β-dimethyl γ-aminobutyric acid, ornithine, and citrulline (Cit). Amino acid side chains $R^3$ optionally includes protected forms of amino acids where reactive functionality of the side chains are protected. Protected amino acid reagents and intermediates are well known, including lysine-protected with acetyl, formyl, triphenylmethyl (trityl), and monomethoxytrityl (MMT). Other protected amino acid units include arginine-protected tosyl or nitro group, ornithine-protected with acetyl or formyl groups.

For Formula I and II compounds, $R^4$ and $R^5$ may together form cyclic boronate esters, such as a pinanediol, pinacol, or catechol, and having the structures:

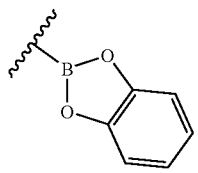

Embodiments of Formula I compounds include those selected from Formula Ia:

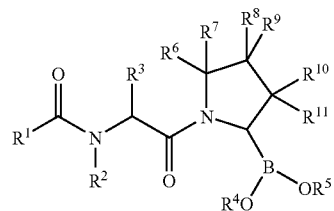

Ia wherein X is C(=O) and $R^{12}$ is H. Exemplary Formula Ia compounds include those selected from Formula Ib:

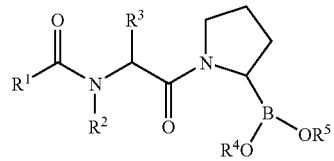

Ib wherein $R^6$, $R^7$, $R^8$, $R^9$, $R^{10}$, $R^{11}$ and $R^{12}$ are each H.

Exemplary Formula Ib compounds include the structures:

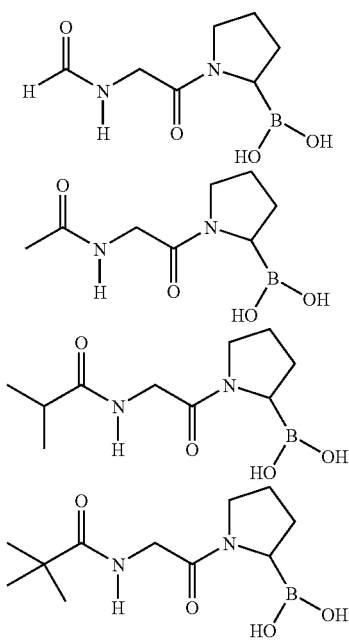

-continued
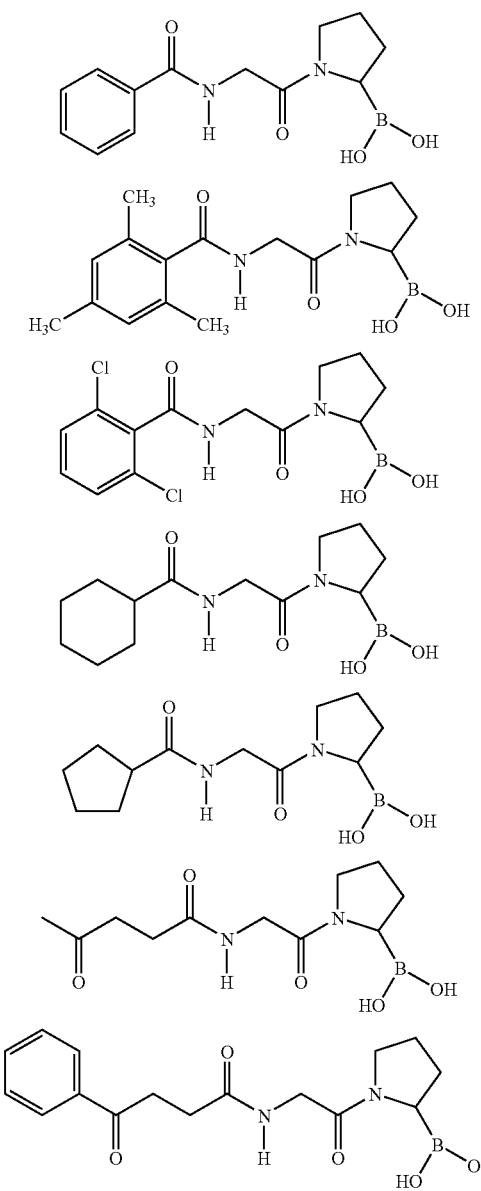
where $R^2$ and $R^3$ are each H.
Exemplary Formula Ib compounds include the structures:
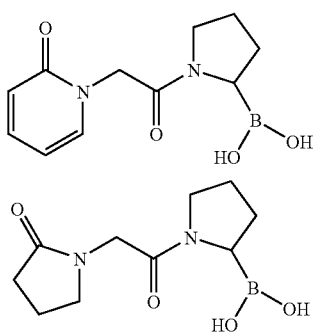
-continued
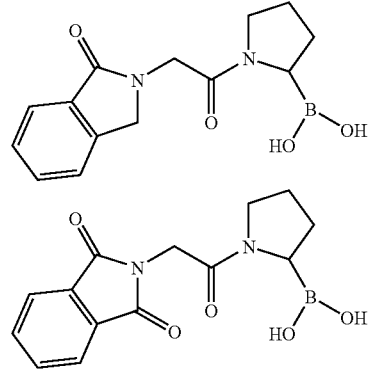
where $R^1$ and $R^2$ form a $C_2$-$C_{20}$ heterocycle;
Exemplary Formula Ib compounds include the structures:
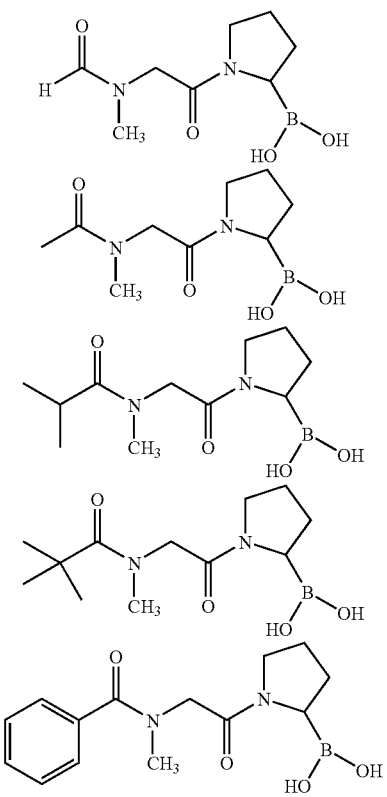
where $R^2$ is methyl and $R^3$ is H.

Exemplary Formula Ib compounds include the structures:
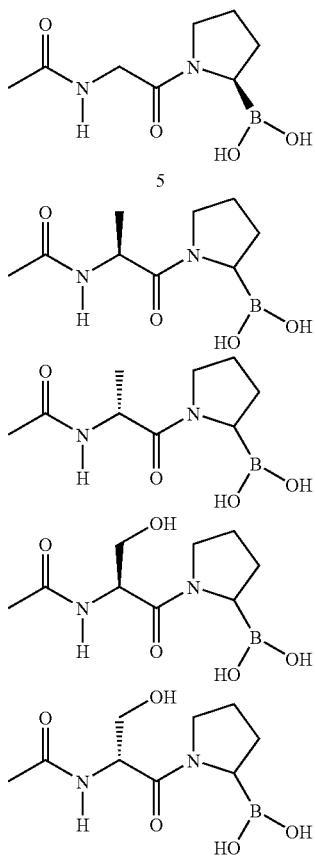
Embodiments of Formula I compounds include those selected from Formula Ic:
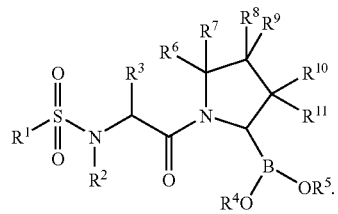
Formula Ic compounds include the structures:
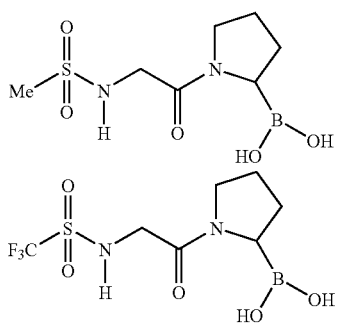
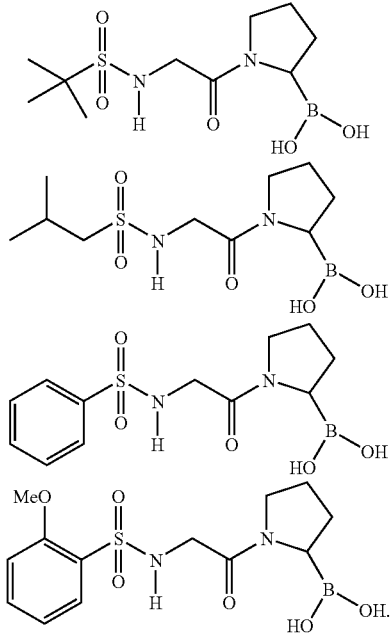
Embodiments of Formula II compounds include those selected from Formulas IIa and IIb:
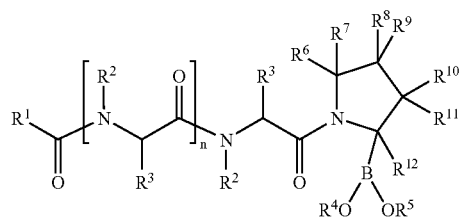
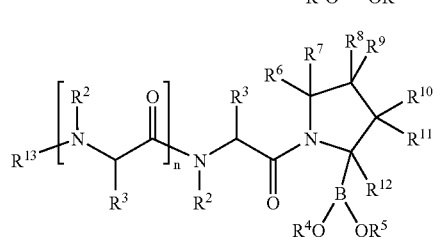
Formula IIa compounds include the structures:
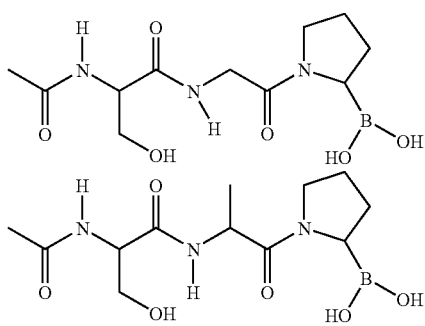

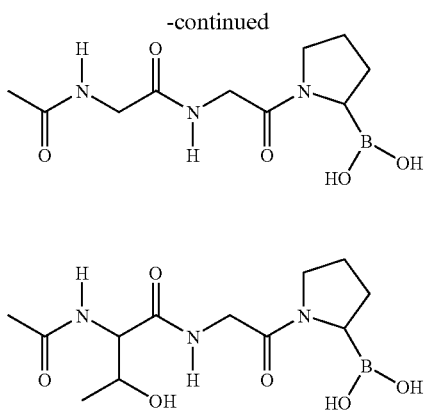

Synthesis of N-Blocked Peptide Proline Boronate Compounds

Peptide compounds may be prepared by conventional methods known in the art and discussed in Example 5. Proline boronate intermediates may be prepared by the methods found in U.S. Pat. Nos. 4,935,493; 5,462,928; 6,355,614; Gao et al (1998) J. Am. Chem. Soc. 120(10):2211-2217; and Gibson et al (2002) Organic Proc. Res. & Dev. 6:814-816; Coutts et al (1996) J. Med. Chem. 39:2087-2094. Many organoboron compounds are commercially available (Aldrich Chemical, St. Louis, Mo.; Boron Molecular Inc, Research Triangle Park, N.C., 27709

N-acetyl-gly-boroproline 5 was prepared from tert-butyl 1-pyrrolidinecarboxylate (N-t-BOC-pyrrolidine, Aldrich), according to the synthetic route of FIG. 1 and Example 6. Metallation of N-t-BOC-pyrrolidine in THF with sec-butyl-lithium was followed by addition of trimethylborate to give 1-(tert-butoxycarbonyl)pyrrolidin-2-yl-2-boronic acid 1. Borate esterification with the single enantiomer, (+)-pinanediol in tert-butyl methyl ether (MTBE) gave pinane ester 2 (Coutts et al (1994) Tetrahedron Letters 35(29):5109-5112; Kelly et al (1993) Tetrahedron 49:1009-1016). Acid hydrolysis of the BOC group and selective crystallization gave (+)-pinane 1-pyrrolidin-2-yl-2-boronate 3. Coupling of 3 and N-acetyl glycine with EDC (N-ethyl-N'-(3-dimethylaminopropyl)carbodiimide), and HOBt (1-hydroxybenzotriazole) gave the pinane borate of N-acetyl-gly-boroproline 4. Borate exchange of 4 with phenylboronic acid gave N-acetyl-gly-boroproline 5.

Labelling of Peptides and Substrates

Labelling of a peptide FAP substrate is typically conducted by mixing an appropriate reactive dye and the peptide to be conjugated in a suitable solvent in which both are soluble, using methods well-known in the art (Hermanson, Bioconjugate Techniques, (1996) Academic Press, San Diego, Calif.), followed by separation of the conjugate from any unconjugated starting materials or unwanted by-products. The dye conjugate can be stored dry or in solution for later use. The dyes may include a reactive linking group at one of the substituent positions for covalent attachment of the dye to another molecule. Reactive linking groups capable of forming a covalent bond are typically electrophilic functional groups capable of reacting with nucleophilic molecules, such as alcohols, alkoxides, amines, hydroxylamines, and thiols. Examples of reactive linking groups include succinimidyl ester, isothiocyanate, sulfonyl chloride, sulfonate ester, silyl halide, 2,6-dichlorotriazinyl, pentafluorophenyl ester, phosphoramidite, maleimide, haloacetyl, epoxide, alkylhalide, allyl halide, aldehyde, ketone, acylazide, anhydride, and iodoacetamide. An exemplary reactive linking group is N-hydroxysuccinimidyl ester (NHS) of a carboxyl group substituent of the dye. The NHS ester of the dye may be preformed, isolated, purified, and/or characterized, or it may be formed in situ and reacted with a nucleophilic group of a peptide, or the like. Typically, the carboxyl form of the dye is activated by reacting with some combination of a carbodiimide reagent, e.g. dicyclohexylcarbodiimide, diisopropylcarbodiimide, or a uronium reagent, e.g. EDC (N-ethyl-N'-(3-dimethylaminopropyl)carbodiimide), TSTU (O-(N-succinimidyl)-N,N,N',N'-tetramethyluronium tetrafluoroborate, HBTU (O-benzotriazol-1-yl)-N,N,N',N'-tetramethyluronium hexafluorophosphate), or HATU (O-(7-azabenzotriazol-1-yl)-N,N,N',N'-tetramethyluronium hexafluorophosphate), an activator, such as 1-hydroxybenzotriazole (HOBt), and N-hydroxysuccinimide to give the NHS ester of the dye. Other activating and coupling reagents include TBTU (2-(1H-benzotriazo-1-yl)-1-1,3,3-tetramethyluronium hexafluorophosphate), TFFH(N,N',N'',N'''-tetramethyluronium 2-fluoro-hexafluorophosphate), PyBOP (benzotriazole-1-yl-oxy-tris-pyrrolidino-phosphonium hexafluorophosphate, EEDQ (2-ethoxy-1-ethoxycarbonyl-1,2-dihydro-quinoline), DCC (dicyclohexylcarbodiimide); DIPCDI (diisopropylcarbodiimide), MSNT (1-(mesitylene-2-sulfonyl)-3-nitro-1H-1,2,4-triazole, and aryl sulfonyl halides, e.g. triisopropylbenzene-sulfonyl chloride.

Energy transfer dyes of a FRET pair include a donor dye which absorbs light at a first wavelength and emits excitation energy in response, an acceptor dye which is capable of absorbing the excitation energy emitted by the donor dye and fluorescing at a second wavelength in response. Dyes may be of any extended conjugation structure, such as a fluorescein, a rhodamine, a diazodiaryl-type, or a cyanine, many of which are commercially available (Molecular Probes Inc., Eugene Oreg.; Sigma Chemical Co., St. Louis, Mo.). A peptide may be labelled with a donor dye and an acceptor dye on opposite sides of the cleavage site of the peptide. Peptides can be labelled at the carboxyl terminus, the amino terminus, or an internal amino acid, e.g. cysteine or lysine side chain (U.S. Pat. No. 5,605,809).

Peptide substrates may be prepared by solution phase or solid-phase methods. Solid-phase methods include synthesis on a solid phase resin by typical solid-phase peptide synthesis methods with t-BOC (Geiser, et al. "Automation of solid-phase peptide synthesis" in Macromolecular Sequencing and Synthesis, Alan R. Liss, Inc., 1988, pp. 199-218) or Fmoc/HBTU chemistries (Fields, G. and Noble, R. (1990) "Solid phase peptide synthesis utilizing 9-fluorenylmethoxycarbonyl amino acids", Int. J. Peptide Protein Res. 35:161-214), on an automated synthesizer such as the Rainin Symphony Peptide Synthesizer (Protein Technologies, Inc., Tucson, Ariz.), or Model 433 (Applied Biosystems, Foster City, Calif.).

Protease Expression and Characterization

DPP-4 exists in serum as a soluble glycoprotein beginning at residue 39 (Durinx, et al. (2000) Eur. J. Biochem. 267: 5608-5613). Recombinant Ser39-DPP-4 and an analogous soluble FAP molecule beginning at amino acid Thr38 were expressed and purified according to Example 1 (Edosada et al (2006) Jour. Biological Chem. 281(11):7437-7444 at page 7438). FAP migrated with an apparent molecular weight of 97 kDa when analyzed by SDS-PAGE under reducing conditions. DPP-4 migrated with a molecular weight of 105-115 kDa under reducing SDS-PAGE conditions. These molecular weights are 15-20 kDa greater than expected based on primary amino acid sequence and decreased upon treatment with N-Glycanase, indicating that each protease is N-glycosylated. To further characterize each protease, molecular weights were determined in solution using multi-angle light scattering in combination with gel filtration chromatography and interferometric refractometry. FAP exists predominantly as a dimer with a molecular weight of 200±15 kDa by electrophoretic mobility relative to standards. Small amounts of monomeric (elution volume 9.0 ml) and multimeric (elution volume<8.0 ml) FAP were also observed. The predominant elution peak of DPP-4 had a molecular weight of 220±15 kDa, indicating a dimeric composition. The dimeric nature of our soluble protease preparations is consistent with the dimeric composition of FAP and DPP-4 crystal structures, suggesting that they are structurally intact (Aertgeerts, et al (2005) J. Biol. Chem. 280(20):19441-19444; Rasmussen, et al (2003) Nature Structural Biology 10(1):19-25; Thoma, et al (2003) Structure 11:947-959; Engel, et al (2003) Proc. Natl. Acad. Sci. USA 100(9):5063-5068; Aertgeerts, et al (2004) Protein Science 13:1-10).

Substrate Specificity of FAP

Cleavage by FAP of model peptide substrates can be detected and quantitated where the peptide is labelled with two moieties, a fluorescent reporter and quencher, which together undergo fluorescence resonance energy transfer (FRET). Cleavage of the FRET peptide releases fluorescence, i.e. ceases quenching. which may be detected and quantitated. The fluorescence of the reporter may be partially or significantly quenched by the quencher moiety in an intact peptide. Upon cleavage of the peptide by a peptidase or protease, a detectable increase in fluorescence may be measured (Knight, C. (1995) "Fluorimetric Assays of Proteolytic Enzymes", Methods in Enzymology, Academic Press, 248: 18-34).

Figure 3:
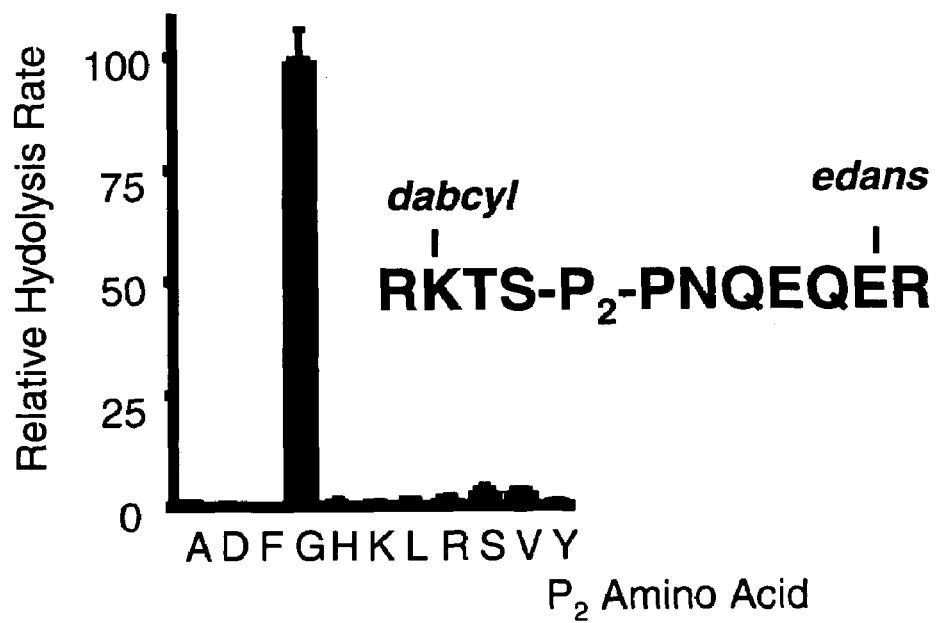
FIG. 3 shows a graph of the relative hydrolysis rates for endopeptidase cleavage of FRET peptide substrates, RK(dabcyl)TS-$P_2$-PNQEQE(edans)R, by FAP where the $P_2$ site is on the N-terminal side of proline was varied with the L-amino acids: alanine, aspartic acid, phenylalanine, glycine, histidine, lysine, leucine, arginine, serine, valine, and tyrosine (from left).

The substrate specificity of FAP was measured with labelled peptide substrates (Edosada et al (2006) Jour. Biological Chem. 281(11):7437-7444). FIG. 3 shows a graph of the relative hydrolysis rates for endopeptidase cleavage of FRET peptide substrates, RK(dabcyl)TS-P$_2$-PNQEQE (edans)R, by FAP. The P$_2$ site is on the N-terminal side of proline and was varied with the L-amino acids: alanine, aspartic acid, phenylalanine, glycine, histidine, lysine, leucine, arginine, serine, valine, and tyrosine (from left). The degree of FAP enzymatic activity in tumors may be determined by an immunocapture assay with coumarin labelled substrates (Cheng et al (2005) Mol. Cancer Ther. 4(3):351-60; Cheng et al (2002) Cancer Res. 62:4767-4772).

Table 1 shows that FAP cleaves the FRET (fluorescence resonance energy transfer) labelled peptide, RK(dabcyl)TS-P$_2$-PNQEQE(edans)R, where glycine, D-alanine, or D-serine is in the P$_2$ amino acid position and the peptides are labelled with the fluorophore edans (5-((2-aminoethyl)amino)naphthalene-1-sulfonic acid, sodium salt) at lysine (K) and the quencher dabcyl (4-((4-(dimethylamino)phenyl)azo)benzoic acid) at glutamic acid (E), in an assay buffer containing 0.1 mg/ml bovine serum albumin.

TABLE 1

| P$_2$ peptide substrate X | K$_m$ (µM) | K$_{cat}$ (S$^{-1}$) | k$_{cat}$/K$_m$ (M$^{-1}$ s$^{-1}$) |
|---|---|---|---|
| Gly | 1.3 ± 0.1 | 16.2 ± 0.1 | 1.2 × 10$^7$ |
| D-Ala | 0.8 ± 0.1 | 1.9 ± 0.1 | 2.5 × 10$^6$ |
| D-Ser | 0.6 ± 0.1 | 2.2 ± 0.4 | 3.5 × 10$^6$ |

FIG. 3 shows a graph of the relative hydrolysis rates of FRET peptide substrates, RK(dabcyl)TS-P$_3$-PNQEQE (edans)R, by FAP. The P$_3$ site is on the N-terminal side of glycine-proline and was varied with the L-amino acids: alanine, aspartic acid, phenylalanine, glycine, histidine, lysine, leucine, arginine, serine, valine, and tyrosine (from left). FIG. 3 shows that FAP activity for cleavage of the model FRET-labelled peptide endopeptidase substrate is highest when glycine is adjacent on the N-terminal side of proline.

Figure 4A:
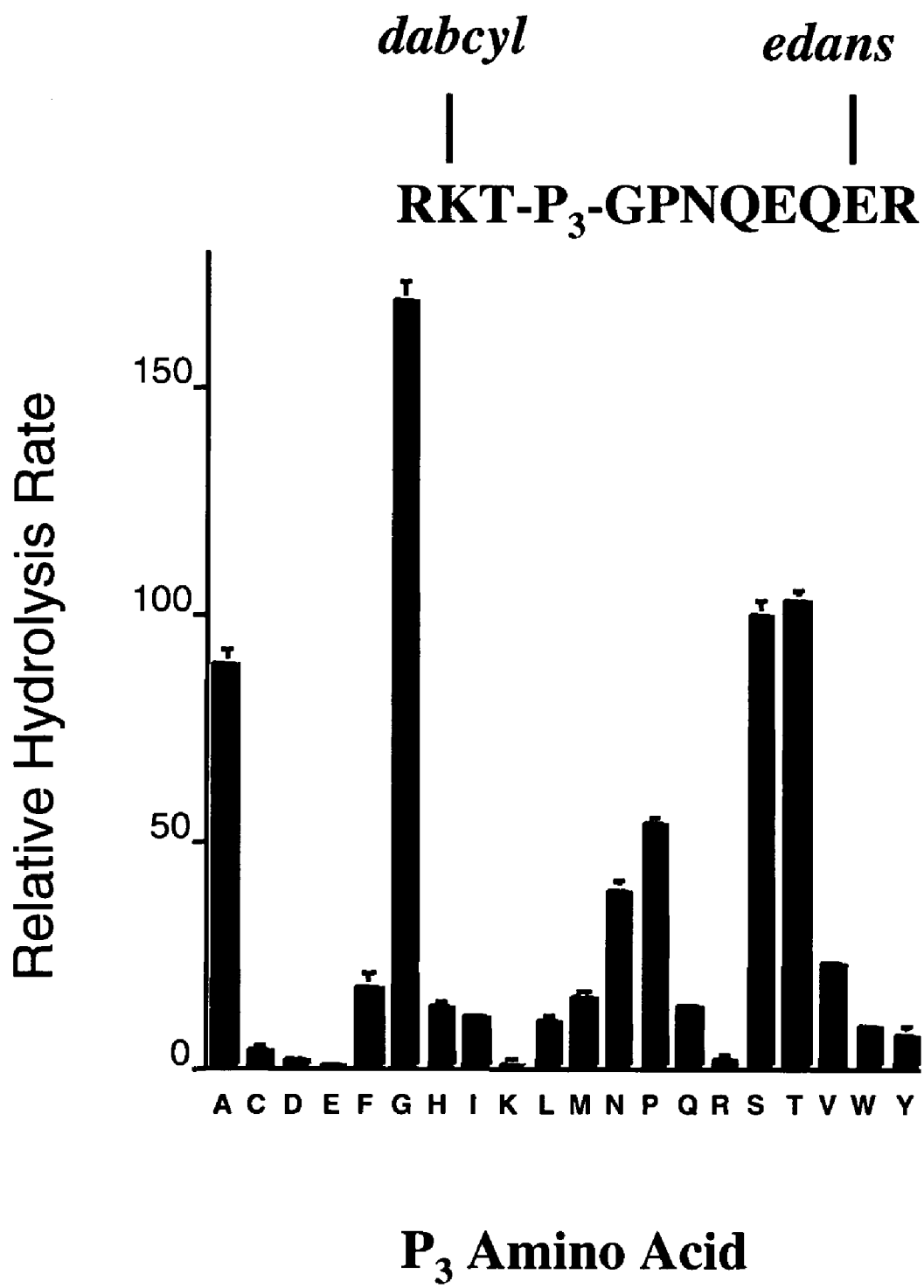
FIG. 4a shows a graph of the relative hydrolysis rates of FRET peptide substrates, RK(dabcyl)T-$P_3$-GPNQEQE(edans)R, by FAP where the $P_3$ site is on the N-terminal side of glycine-proline was varied with the L-amino acids: alanine, cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine (from left).

FIG. 4a shows a graph of the relative hydrolysis rates of FRET peptide substrates, RK(dabcyl)T-P$_3$-GPNQEQE (edans)R, by FAP. The P$_3$ site is on the N-terminal side of glycine-proline and was varied with the L-amino acids: alanine, aspartic acid, phenylalanine, histidine, leucine, lysine, arginine, serine, valine, and tyrosine (from left). FIG. 4a shows that FAP activity for cleavage of the model FRET-labelled peptide endopeptidase substrate is highest when glycine, serine, or threonine are adjacent on the N-terminal side of glycine-proline.

Figure 4B:
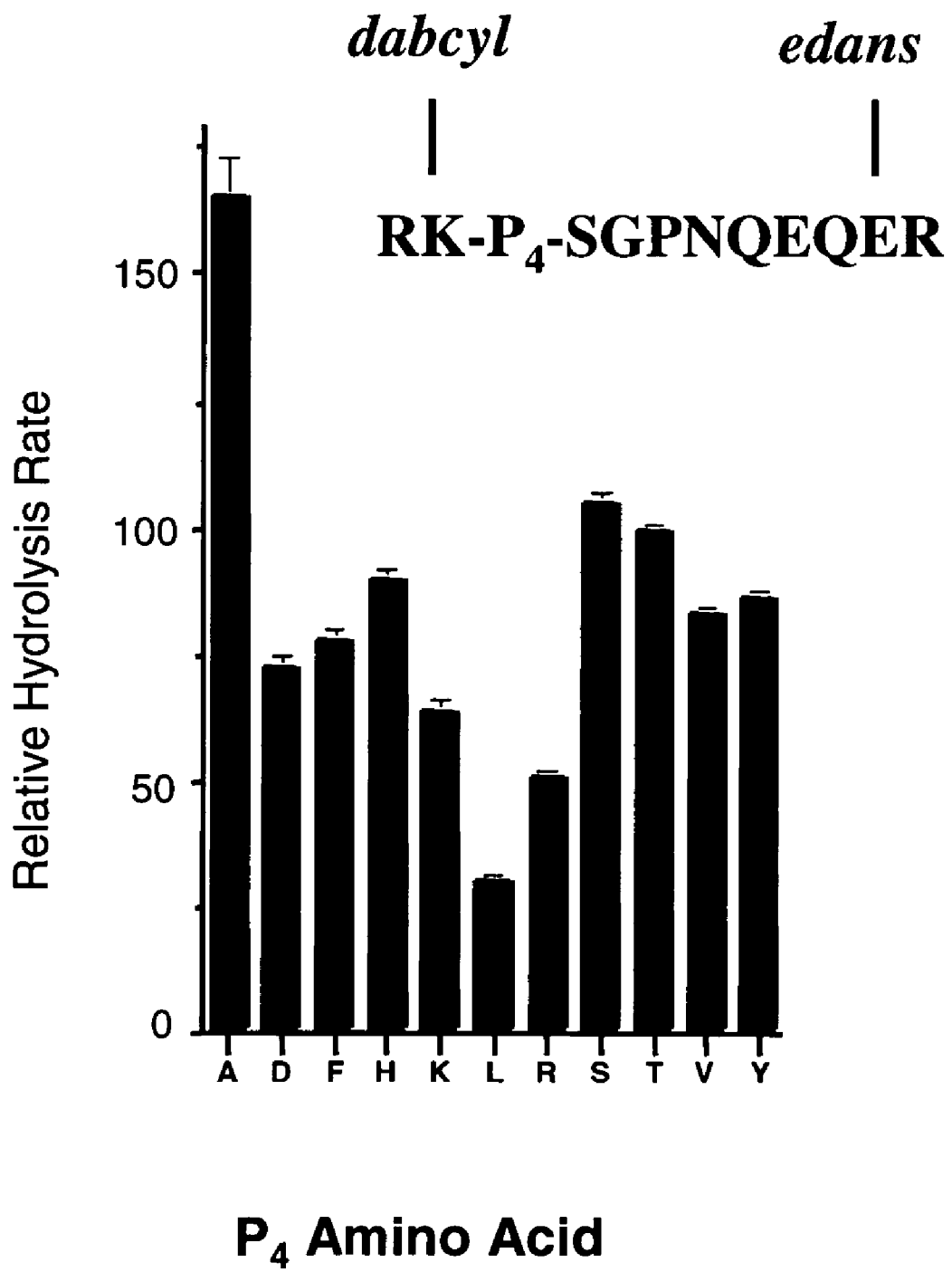
FIG. 4b shows a graph of the relative hydrolysis rates of FRET peptide substrates, RK(dabcyl)-$P_4$-SGPNQEQE(edans)R, by FAP where the $P_4$ site is on the N-terminal side of serine-proline was varied with the L-amino acids: alanine, aspartic acid, phenylalanine, histidine, lysine, leucine, arginine, serine, threonine, valine, and tyrosine (from left).

FIG. 4b shows a graph of the relative hydrolysis rates of FRET peptide substrates, RK(dabcyl)-P$_4$-SGPNQEQE (edans)R, by FAP. The P$_4$ site is on the N-terminal side of serine-proline and was varied with the L-amino acids: alanine, aspartic acid, phenylalanine, histidine, lysine, leucine, arginine, serine, threonine, valine, and tyrosine (from left). FIG. 4b shows that FAP activity for cleavage of the model FRET-labelled peptide endopeptidase substrate is highest when alanine is adjacent on the N-terminal side of serine-glycine-proline.

Figure 4C:
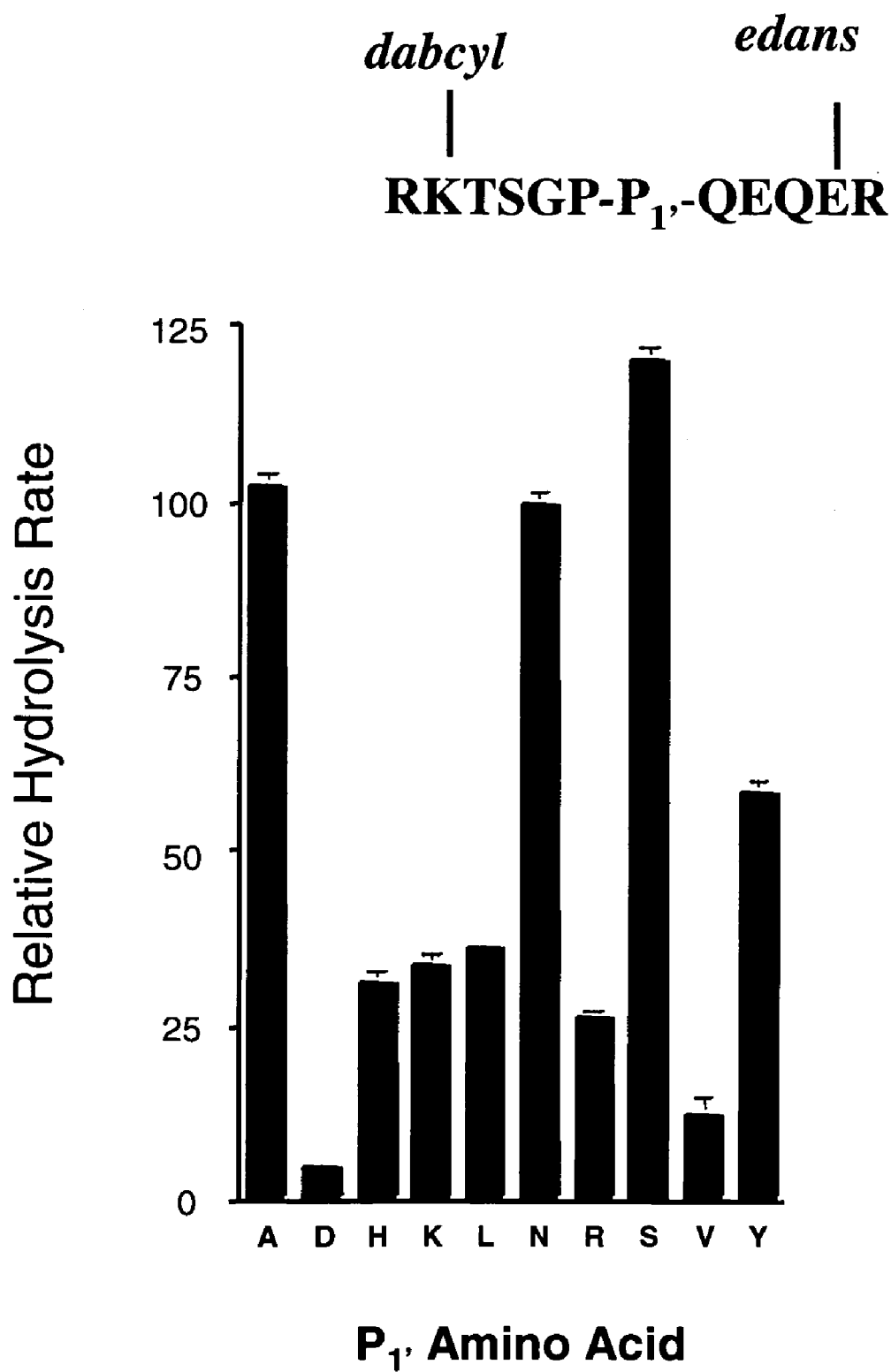
FIG. 4c shows a graph of the relative hydrolysis rates of FRET peptide substrates, RK(dabcyl)TSGP-$P_{1'}$-QEQE(edans)R, by FAP where the $P_{1'}$ site is on the C-terminal side of glycine-proline was varied with the L-amino acids: alanine, aspartic acid, histidine, lysine, leucine, asparagine, arginine, serine, valine, and tyrosine (from left).

FIG. 4c shows a graph of the relative hydrolysis rates of FRET peptide substrates, RK(dabcyl)TSGP-P$_1$'-QEQE(edans)R, by FAP where the P$_1$' site is on the C-terminal side of glycine-proline was varied with the L-amino acids: alanine, aspartic acid, histidine, lysine, leucine, asparagine, arginine, serine, valine, and tyrosine (from left). FIG. 4c shows that FAP activity for cleavage of the model FRET-labelled peptide endopeptidase substrate is highest when alanine, asparagine, serine or tyrosine are adjacent on the C-terminal side of serine-glycine-proline.

Figure 4D:
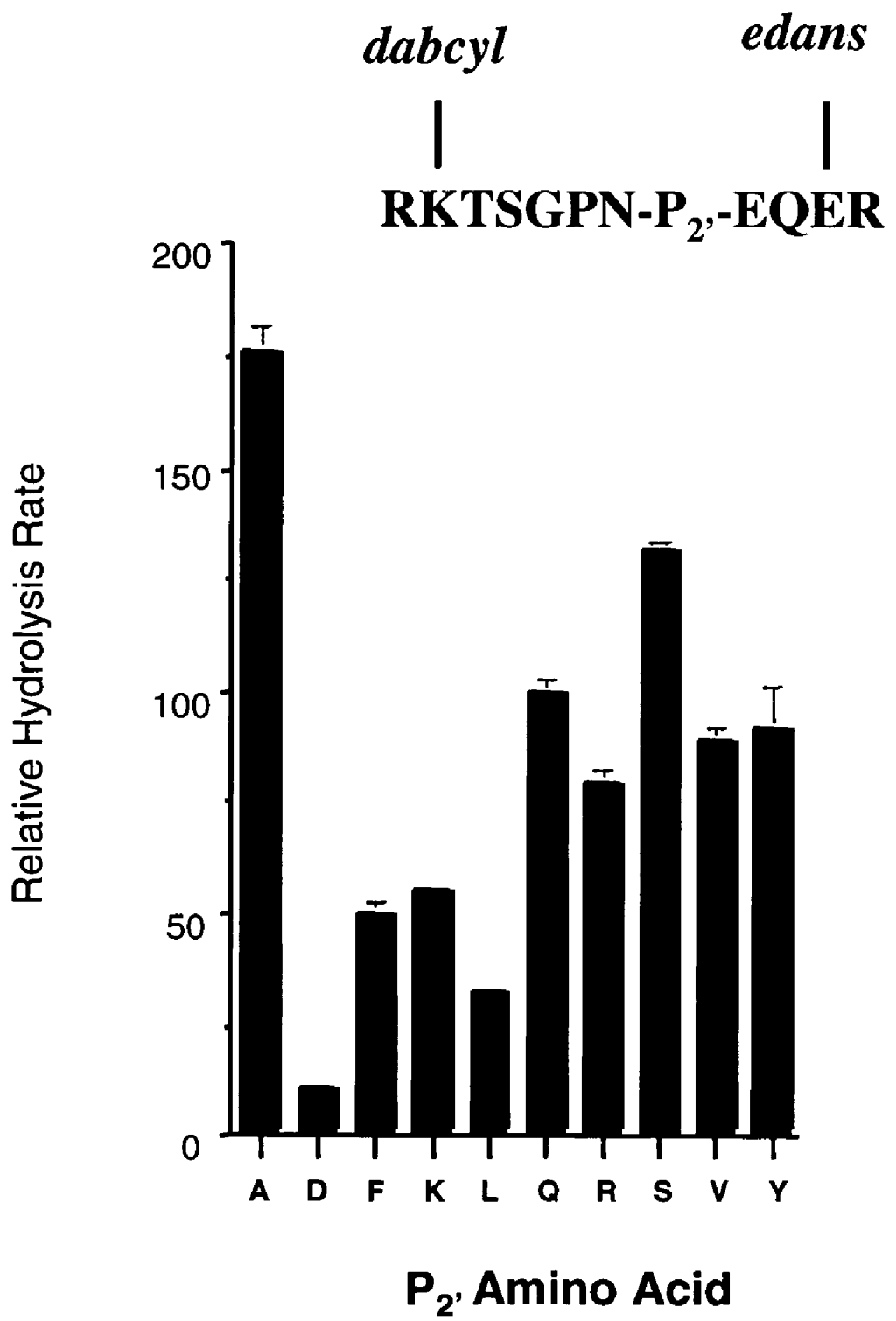
FIG. 4d shows a graph of the relative hydrolysis rates of FRET peptide substrates, RK(dabcyl)TSGPN-$P_{2'}$-EQE(edans)R, by FAP where the $P_{2'}$ site is on the C-terminal side of glycine-proline was varied with the L-amino acids: alanine, aspartic acid, phenylalanine, lysine, leucine, glutamine, arginine, serine, valine, and tyrosine (from left).

FIG. 4d shows a graph of the relative hydrolysis rates of FRET peptide substrates, RK(dabcyl)TSGPN-P$_2$'-EQE(edans)R, by FAP where the P$_2$' site is on the C-terminal side of glycine-proline was varied with the L-amino acids: alanine, aspartic acid, phenylalanine, lysine, leucine, glutamine, arginine, serine, valine, and tyrosine (from left). FIG. 4d shows that FAP activity for cleavage of the model FRET-labelled peptide endopeptidase substrate is highest when alanine, glutamine, or serine are adjacent on the C-terminal side of serine-glycine-proline-asparagine.

Differential Activities of FAP and Dipeptidyl Peptidases

Figure 2:
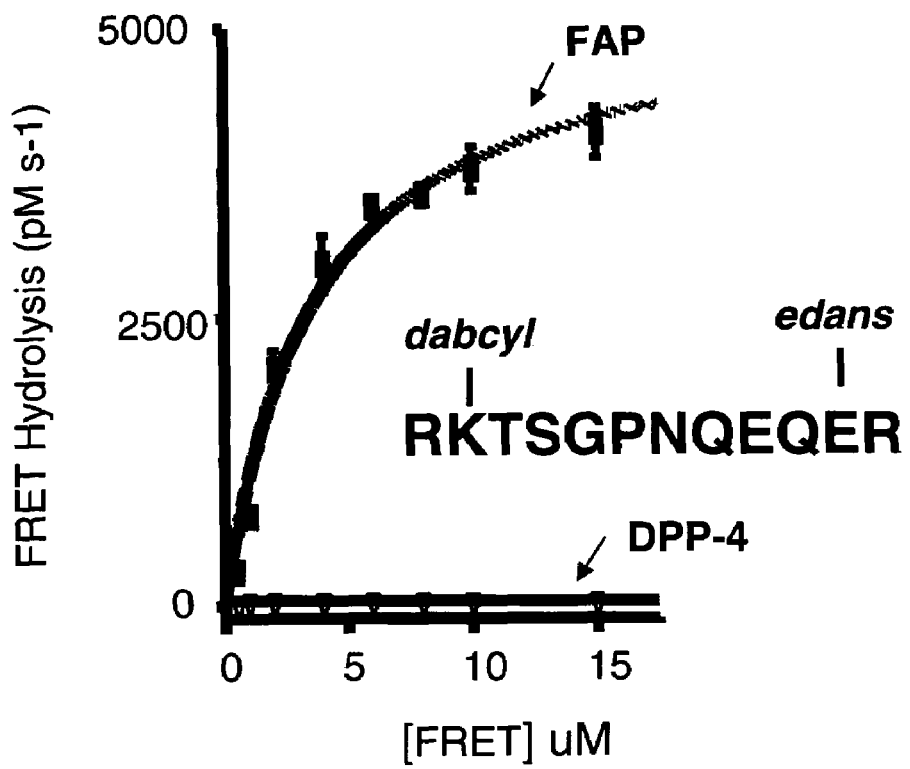
FIG. 2 shows a graph of the relative rate of hydrolysis of a FRET-labelled FAP substrate peptide, RK(dabcyl)TSGPN-QEQE(edans)R, by FAP and DPP-4.

FIG. 2 shows a graph of the relative rate of hydrolysis of a FRET-labelled FAP substrate peptide, RK(dabcyl)TSGPN-QEQE(edans)R, by FAP and DPP-4. FIG. 2 shows that FAP cleaves endopeptidase substrates such as the FRET-labelled peptide, whereas DPP-4 does not.

FAP Cleavage of Model Coumarin-Labelled Peptide Substrates

The relative cleavage rates of a variety of N-blocked, C-terminal coumarin (AMCC) Gly-Pro dipeptide substrates 6 were measured. The rates were normalized to N-unblocked Gly-Pro-AMCC for FAP and DPP-4. Table 2 shows that the N-blocked variants are not cleavage substrates for DPP-4, but they are cleaved by FAP.

TABLE 2

6

| R$^1$—X 6 | FAP | DPP-4 |
| --- | --- | --- |
| (H) Gly-Pro-AMCC | 100 | 100 |
| HC(=O) | 130 | 7 |
| CH$_3$C(=O) | 100 | 0 |
| HO$_2$CCH$_2$CH$_2$C(=O) | 0 | 0 |
| PhCH$_2$OC(=O) (Z) | 42 | 0 |
| 5-carboxyfluorescein | 36 | 0 |
| biotin | 40 | 0 |

To examine whether FAP could cleave other N-substituted-Gly-Pro-based substrates, N-methyl-, formyl-, succinyl-, benzyloxycarbonyl-(Z-) and biotinyl-Gly-Pro-AMCC substrates 6 were synthesized and reacted with FAP (37 nM) and DPP-4 (6.8 nM). With the exception of succinyl-Gly-Pro-AMCC, FAP cleaved all N-substituted-Gly-Pro-AMCC substrates 6 at rates 35-150% of the normalized rate for Gly-Pro-AMCC hydrolysis (Table 2), indicating that the protease tolerates other N-terminal blocking groups. Kinetic analysis with commercially available Z-Gly-Pro-AMC (Table 5) showed a catalytic efficiency about 3-fold lower than that for Gly-Pro-AFC (Table 4), consistent with these results. In contrast with FAP, DPP-4 cleaved only N-methyl-Gly-Pro-AMCC at a rate comparable to Gly-Pro-AMCC. A low rate of hydrolysis was obtained with formyl-Gly-Pro-AMCC substrates but no cleavage of succinyl-, Z-, or biotinyl-Gly-Pro-AMCC substrates was observed at concentrations up to 1 mM, indicating that DPP-4 does not tolerate N-acyl-Gly-Pro-based substrates. DPP-4 also showed little activity against commercially available Z-Gly-Pro-AMC (Table 5).

The relative cleavage rates by FAP and several dipeptidases of N-blocked (8) and unblocked (7) Gly-Pro dipeptide substrates were measured. The relative activities shown in Table 3 demonstrate that dipeptidases DPP-4, DPP-7, DPP-8, and DPP-9 prefer the unblocked substrate, whereas FAP is not so specific, cleaving 7 and 8 at the same rate.

TABLE 3

7

Gly-Pro-AFC

8

Ac-Gly-Pro-AFC

| Protease | Relative Activity Gly-Pro-AFC 7/Ac-Gly-Pro-AFC 8 |
| --- | --- |
| FAP | 1.0 |
| DPP-4 | 10,000 |
| DPP-7 | 200 |
| DPP-8 | 33 |
| DPP-9 | 10,000 |
| APH | no cleavage |

Figure 6:
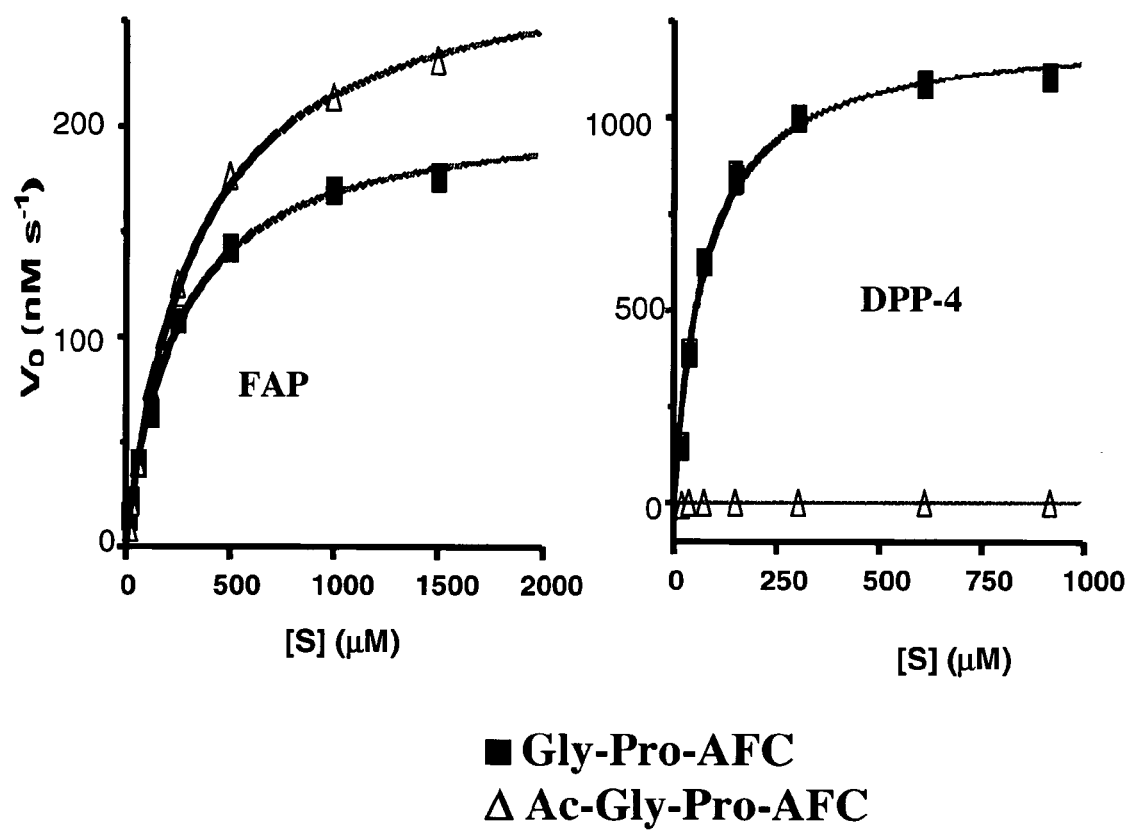
FIG. 6 shows graphs of the cleavage rate velocity $V_0$ of nanomolar/sec by FAP at 37 nM and DPP-4 at 10.5 nM of the blocked (Ac-Gly-Pro-AFC) and unblocked (Gly-Pro-AFC) dipeptide substrates at various concentrations of the substrates. AFC=2-(7-amino-4-(trifluoromethyl)-2-oxo-2H-chromen-3-yl)acetamide (Sigma Chemical Co., coumarin 151, 7-amido-4-trifluoromethyl coumarin). Each value represents the average±SEM (n=3).

The effect of blocking the amino terminus of a dipeptide proline substrate was measured in cleavage by FAP and DPP-4. FIG. 6 shows graphs of the cleavage rate velocity V$_0$ of nanomolar/sec by FAP and DPP-4 of the blocked (Ac-Gly-Pro-AFC 8) and unblocked (Gly-Pro-AFC 7) dipeptide substrates at various concentrations (Edosada et al (2006) Jour. Biological Chem. 281(11):7437-7444 at page 7440). AFC=2-(7-amino-4-(trifluoromethyl)-2-oxo-2H-chromen-3-yl)acetamide (Sigma Chemical Co., coumarin 151, 7-amido-4-trifluoromethyl coumarin). FAP cleaves Ac-Gly-Pro-AFC 8 and Gly-Pro-AFC 7 at comparable rates. DPP-4 cleaves Gly-Pro-AFC 7, but not Ac-Gly-Pro-AFC 8. The relative rate of cleavage (k$_{cat}$/K$_m$) of the blocked to unblocked substrates for FAP is 1.1 and for DPP-4 is about 0.00002. DPP-4 has little activity against Ac-Gly-Pro-AFC 8.

Figure 5:
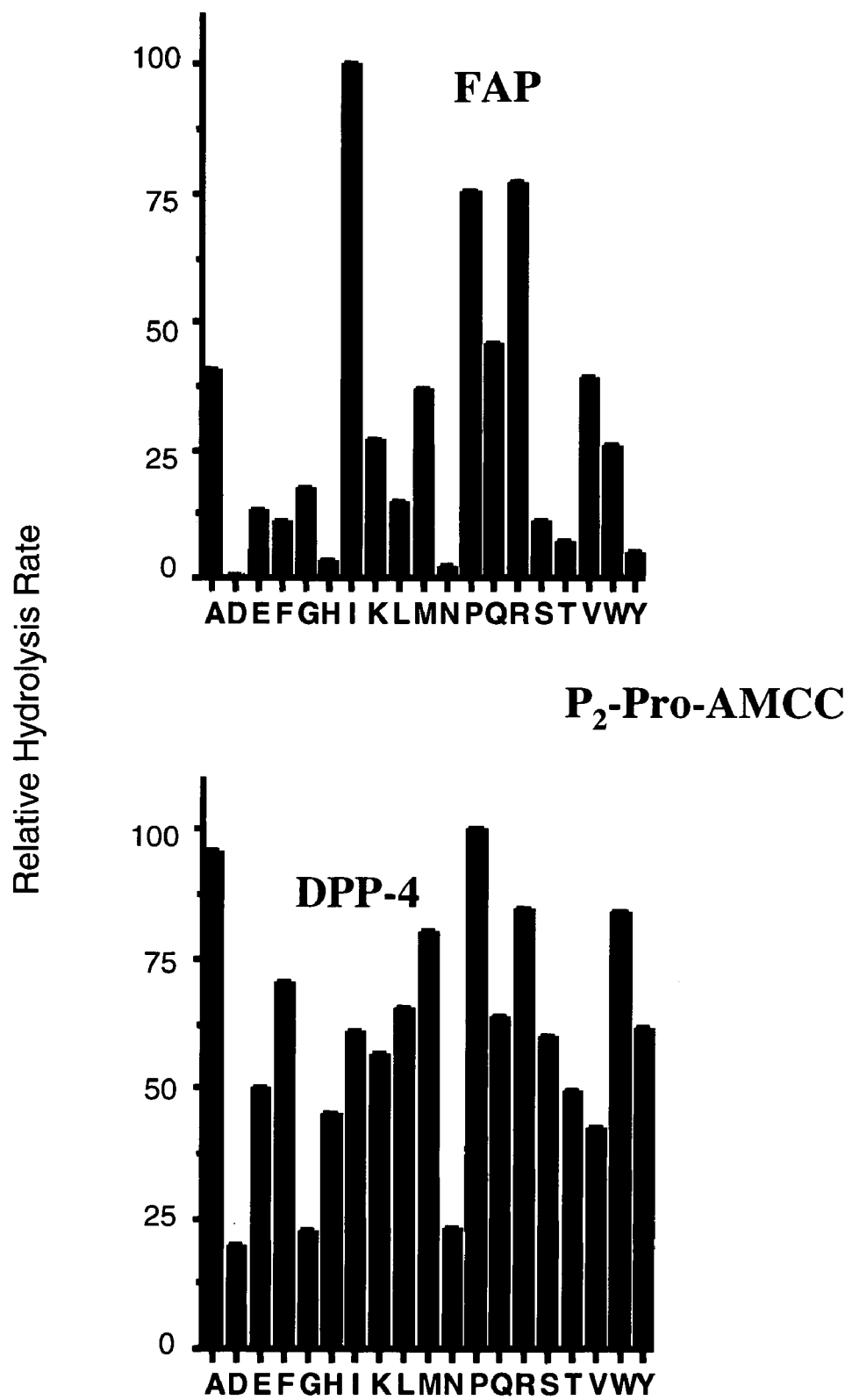
FIG. 5 shows a graph of the relative hydrolysis rates of model coumarin-labelled dipeptide substrates, $P_2$-Pro-AMCC, by FAP at 37 nM (top) and DPP-4 at 6.8 nM (bottom). Amino-terminus $P_2$ was varied with the L-amino acids: alanine, aspartic acid, glutamic acid, phenylalanine, glycine, histidine, isoleucine, lysine, leucine, methionine, asparagine, proline, glutamine, arginine, serine, threonine, valine, tryptophan, and tyrosine (shown by one-letter code, from left). AMCC=2-(7-amino-4-methyl-2-oxo-2H-chromen-3-yl)acetamide.

The cleavage (hydrolysis) rates of various C-terminal coumarin dipeptide substrates 7-16 by FAP and DPP-4 were measured (Tables 4 and 5). The amino-terminus of the substrates was unblocked and the amino acids were varied in Table 4. The amino-terminus of the substrates was blocked and the amino acids were varied in Table 5. To extend the results obtained with the dipeptide substrate library, kinetic parameters were determined for cleavage of the unblocked dipeptide substrates by FAP (Table 4). The catalytic efficiency ($k_{cat}/K_m$) for substrate cleavage was greatest with Ile-Pro-AFC, followed by Ala-Pro-, Gly-Pro- and Phe-Pro-AFC, consistent with the dipeptide substrate library results (FIG. 5). With the exception of Ile-Pro-AFC, these differences reflect differences in $k_{cat}$ values, as the $K_m$ for each substrate was ~250 μM. The greater catalytic efficiency observed for Ile-Pro-AFC hydrolysis was due to both $k_{cat}$ and $K_m$ effects as the observed $K_m$ was ~2.5-fold lower than the other $P_2$-Pro-AFC substrates. FAP showed markedly less activity against $P_2$-Ala-based substrates. Gly-Ala-AMC was not cleaved and the catalytic efficiency for Lys-Ala-AFC cleavage was 400-1000-fold less than the catalytic efficiency for cleavage of $P_2$-Pro-based peptides (Table 4), indicating that FAP prefers Pro in the $P_1$ position. Kinetic constants for cleavage of Ala-Pro-AFC and Gly-Pro-AFC by DPP-4 were determined (Table 4). The catalytic efficiency for Ala-Pro-AFC hydrolysis was greater than that for Gly-Pro-AFC, and consistent with the dipeptide library. Strikingly, the catalytic efficiencies for dipeptide hydrolysis by DPP-4 were consistently ~100-fold greater than observed with FAP, reflecting both an increase in $k_{cat}$ and decrease in $K_m$.

TABLE 4

Kinetic constants (avg. standard error, n ≥ 3) for hydrolysis of dipeptide substrates with unblocked N-termini by FAP and DPP-4

| Protease | substrate[a] | $K_m$ (μM) | Kcat (s$^{-1}$) | $K_{cat}/K_m$ (M$^{-1}$ s$^{-1}$) |
|---|---|---|---|---|
| FAP | Gly-Pro-AFC 7 | 248 ± 12 | 5.6 ± 0.2 | 2.3 × 10$^4$ |
| FAP | Ala-Pro-AFC 9 | 244 ± 28 | 14.2 ± 0.9 | 5.8 × 10$^4$ |
| FAP | Phe-Pro-AFC 10 | 245 ± 22 | 1.1 ± 0.1 | 4.5 × 10$^3$ |
| FAP | Gly-Ala-AMC 11 | NC[b] | NC | NC |
| FAP | Lys-Ala-AMC 12 | 189 ± 20 | 0.01 ± 0.001 | 53 |
| FAP | Ile-Pro-AFC 13 | 106 ± 6 | 6.9 ± 0.3 | 6.4 × 10$^4$ |
| DPP-4 | Gly-Pro-AFC 7 | 76 ± 10 | 121 ± 5 | 1.6 × 10$^6$ |
| DPP-4 | Ala-Pro-AFC 9 | 16 ± 3 | 45.6 ± 1.7 | 2.9 × 10$^6$ |

[a]substrate cleavage conducted at 23° C. in 50 mM Tris-HCl, 100 mM NaCl, 1 mM EDTA, pH 7.4
[b]no cleavage up to 1 mM substrate

TABLE 5

Kinetic constants (avg. standard error, n ≥ 3) for hydrolysis of dipeptide substrates with blocked N-termini by FAP and DPP-4

| Protease | substrate[a] | $K_m$ (μM) | Kcat (s$^{-1}$) | $K_{cat}/K_m$ (M$^{-1}$ s$^{-1}$) |
|---|---|---|---|---|
| FAP | Ac-Gly-Pro-AFC 8 | 330 ± 3 | 7.7 ± 0.2 | 2.3 × 10$^4$ |
| FAP | Z-Gly-Pro-AMC 14 | >4 | <30 | 7.4 ± 0.6 × 10$^{3b}$ |
| FAP | Ac-Ala-Pro-AFC 15 | NC[d] | NC | NC |
| FAP | Z-Ala-Pro-MNA 16 | NC | NC | NC |
| DPP-4 | Ac-Gly-Pro-AFC 8 | >2 | <0.07 | 36 ± 3[c] |
| DPP-4 | Z-Gly-Pro-AMC 14 | NC | NC | NC |
| DPP-4 | Ac-Ala-Pro-AFC 15 | NC[d] | NC | NC |
| DPP-4 | Z-Ala-Pro-MNA 16 | NC | NC | NC |

[a]substrate cleavage conducted at 23° C. in 50 mM Tris-HCl, 100 mM NaCl, 1 mM EDTA, pH 7.4
[b]determined under first order conditions, 30 nM FAP, 125 μM substrate
[c]determined under first order conditions, 200 nM DPP-4, 250 μM substrate
[d]no cleavage up to 1 mM substrate
Ac = CH$_3$C(=O);
Z = PhCH$_2$OC(=O);
AMC = 7-amino-4-methyl-coumarin;
AFC = 7-amino-4-trifluoromethylcoumarin;
MNA = 4-methoxy-2-naphthylamine FIG. 5 shows a graph of the relative hydrolysis rates of model coumarin-labelled dipeptide substrates, $P_2$-Pro-AMCC, by FAP (top) and DPP-4 (bottom). Amino-terminus $P_2$ was varied with the L-amino acids: alanine, aspartic acid, glutamic acid, phenylalanine, glycine, histidine, isoleucine, lysine, leucine, methionine, asparagine, proline, glutamine, arginine, serine, threonine, valine, tryptophan, and tyrosine (from left). AMCC=2-(7-amino-4-methyl-2-oxo-2H-chromen-3-yl)acetamide. For both enzymes, the amino acid adjacent in the model dipeptide substrate had little effect where the amino-terminus was unblocked. Hydrolysis rates of other $P_2$-Pro-AMCC substrates by FAP and DPP-4 relative to Gly-Pro-AMCC include the following in Table 6:

TABLE 6

Relative Hydrolysis rates of $P_2$-Pro-AMCC substrates by FAP and DPP-4

| $P_2$ ($P_2$-Pro-AMCC) | FAP* | DPP-4* |
|---|---|---|
| Gly | 100 | 100 |
| cyclohexyl gly | 1137 | 38 |
| Ac-Cyclohexyl Gly | 0 | 0 |
| D-Ala | 0 | 2 |
| Ac-(D-Ala) | 3 | 1 |
| Ac-(D-Ser) | 3 | 0 |
| β-Ala | 2 | 1 |

*hydrolysis rates normalized to Gly-Pro-AMCC

Inhibition of FAP and DPP-4 activity against Ala-Pro-AFC by $P_2$-Pro-AMCC compounds was measured at various concentration of the $P_2$-Pro-AMCC compounds in Table 7.

TABLE 7

Relative Hydrolysis rates of $P_2$-Pro-AMCC substrates by FAP and DPP-4

| $P_2$ ($P_2$-Pro-AMCC) | FAP $K_i$ (nM) | DPP-4 $K_i$ (nM) |
|---|---|---|
| Ac-cyclohexyl Gly | 67 | >1000 |
| D-Ala | 711 | >2000 |
| Ac-(D-Ala) | 1000 | >2000 |
| Ac-(D-Ser) | 200 | >2000 |
| β-Ala | 340 | 2000 |

Figure 7:
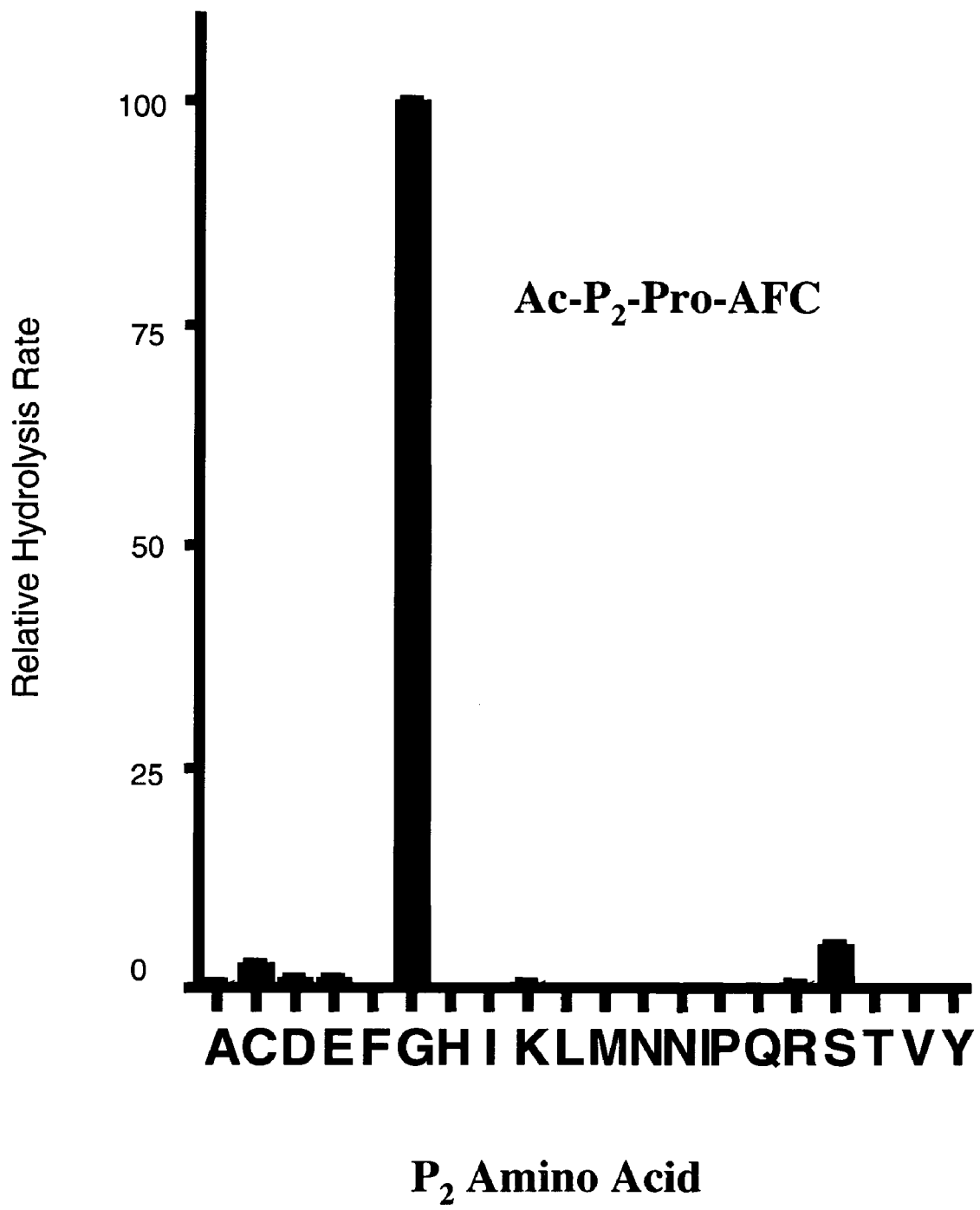
FIG. 7 shows a graph of the relative hydrolysis rates of model coumarin-labelled dipeptide substrates, Ac-$P_2$-Pro-AFC, by FAP. Amino-terminus $P_2$ was varied with the L-amino acids: alanine, cysteine, aspartic acid, glutamic acid, phenylalanine, glycine, histidine, isoleucine, lysine, leucine, methionine, asparagine, nor-leucine, proline, glutamine, arginine, serine, threonine, valine, and tyrosine (from left).

The effect of varying the amino acid at the amino terminus of N-blocked dipeptide proline substrates on cleavage by FAP was measured. FIG. 7 shows a graph of the relative hydrolysis rates of model coumarin-labelled dipeptide substrates, Ac-$P_2$-Pro-AFC, by FAP. Amino-terminus $P_2$ was varied with the L-amino acids: alanine, cysteine, aspartic acid, glutamic acid, phenylalanine, glycine, histidine, isoleucine, lysine, leucine, methionine, asparagine, nor-leucine, proline, glutamine, arginine, serine, threonine, valine, and tyrosine (from left). The rate of cleavage by Ac-Gly-Pro-AFC was far higher than the others. Cysteine, aspartic acid, glutamic acid, and serine substituted variants showed some cleavage activity. DPP-4 has no activity against the Ac-$P_2$-Pro-AFC compounds of FIG. 7. These data suggest that DPP-4 has limited endopeptidase activity and that FAP endopeptidase activity is restricted to Gly-Pro-containing substrates.

Figure 8:
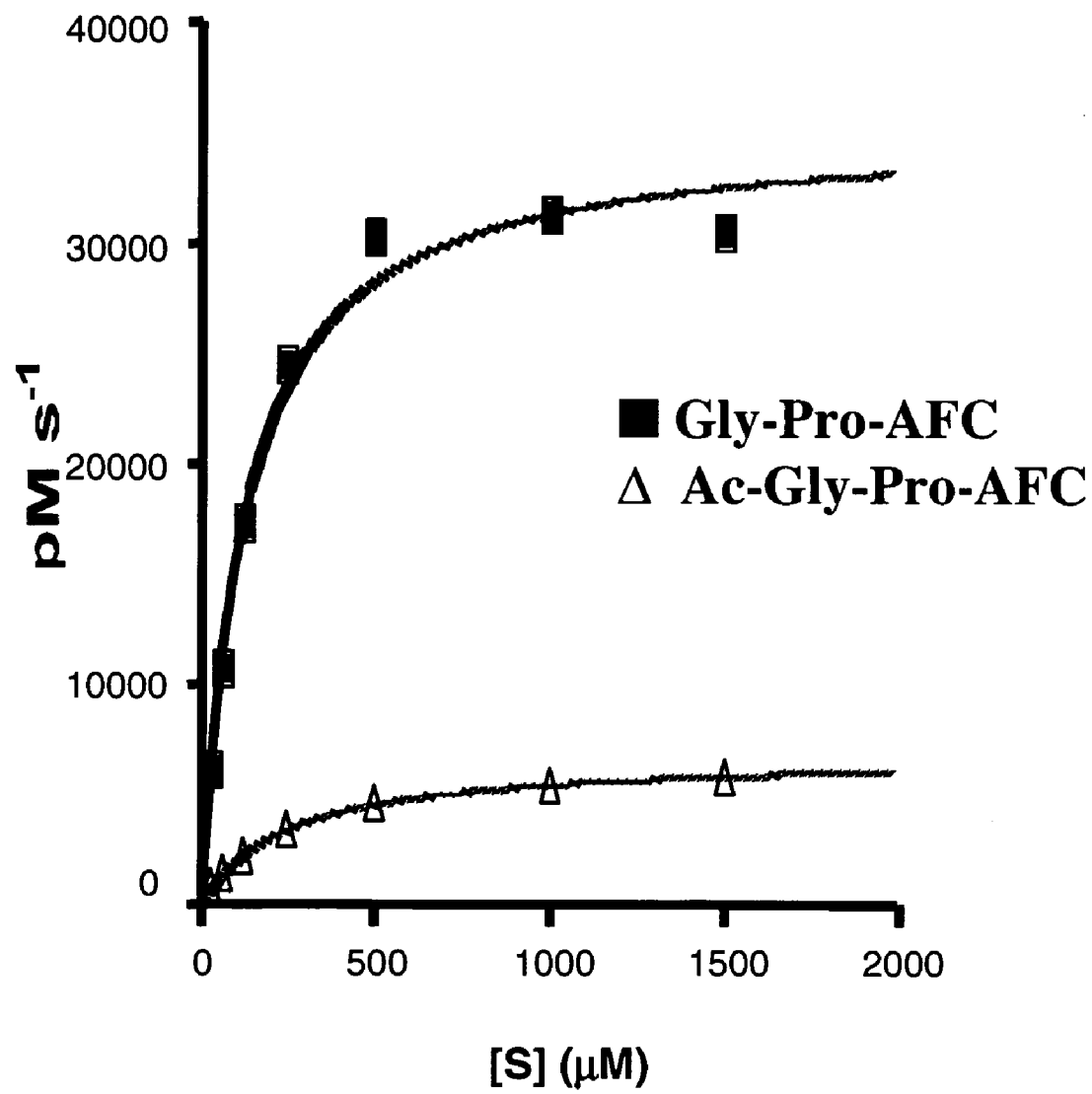
FIG. 8 shows a graph of cleavage by a chimera protease enzyme, (DPP-4)$_{BP}$-(FAP)$_{cat}$, of the blocked (Ac-Gly-Pro-AFC) and unblocked (Gly-Pro-AFC) dipeptide substrates.

FIG. 8 shows a graph of cleavage by a chimera protease enzyme, (DPP-4)$_{BP}$-(FAP)$_{cat}$, of a blocked (Ac-Gly-Pro-AFC 8) and an unblocked (Gly-Pro-AFC 7) dipeptide substrate.

Figure 9:
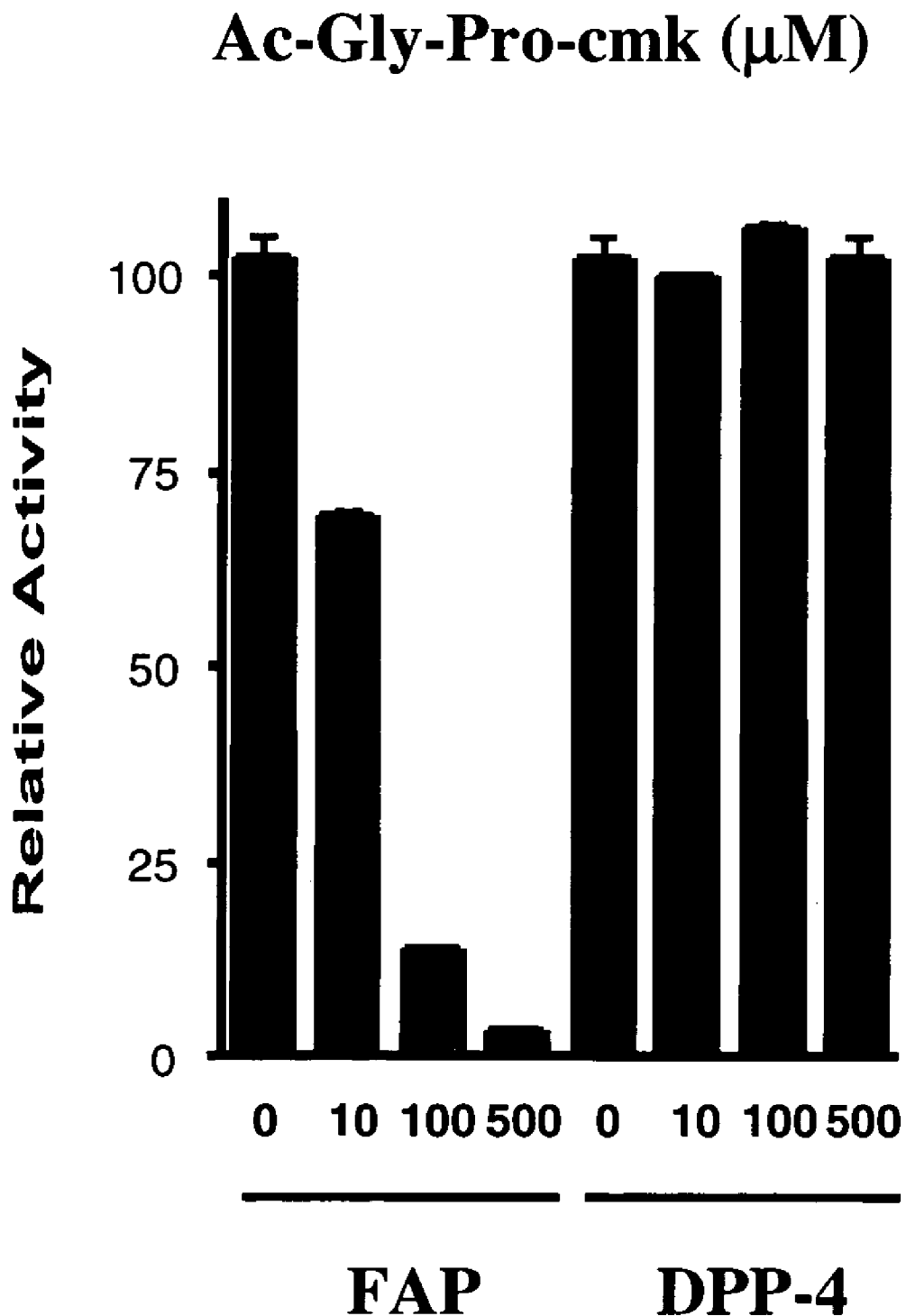
FIG. 9 shows a graph of relative activities of recombinant FAP and recombinant DPP-4 in cleavage of substrate L-Ala-Pro-AFC in the presence of the irreversible inhibitor Ac-Gly-Pro-cmk at different concentrations of 10, 100, and 500 µM Ac-Gly-Pro-cmk, and negative control (0 µM). cmk=chloromethyl ketone, —C(=O)CH$_2$Cl.
Figure 10:
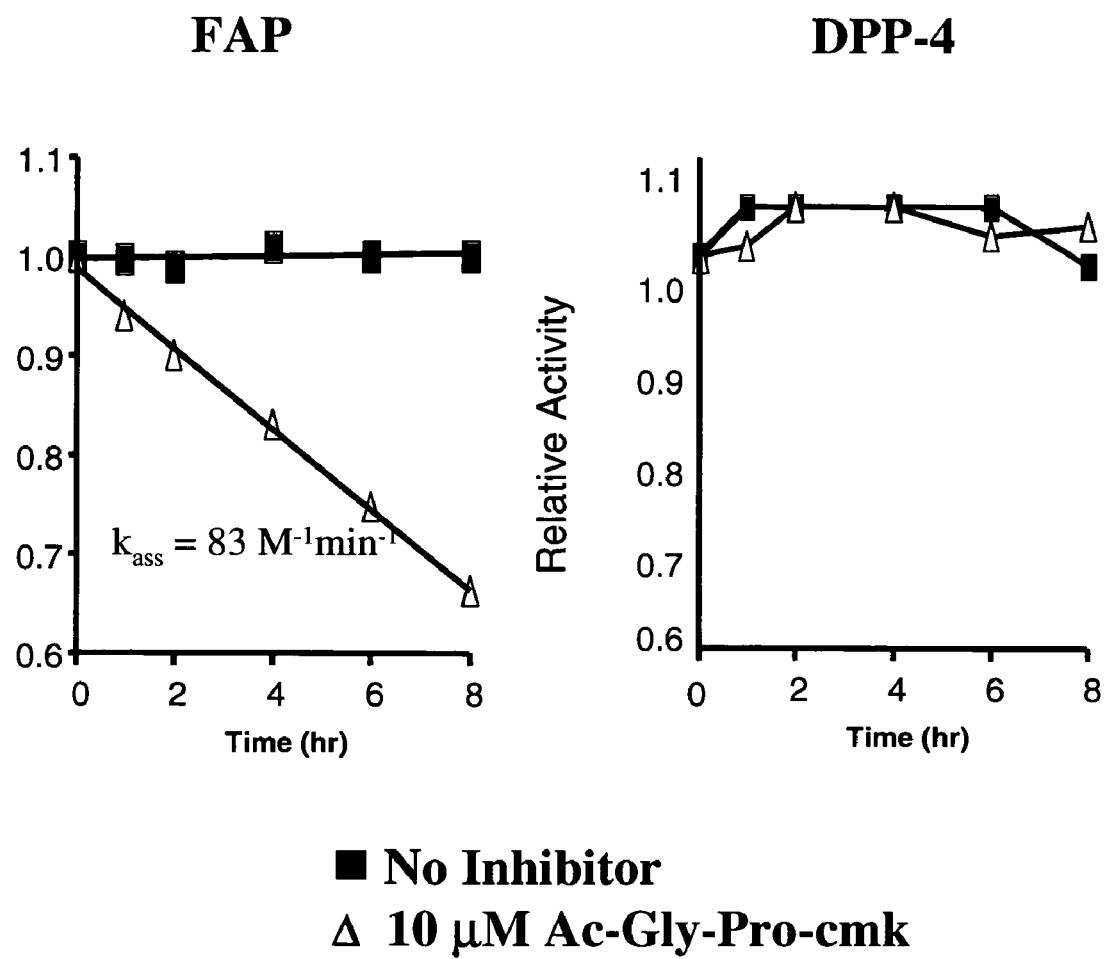
FIG. 10 shows a graph of the time course of cleavage of substrate L-Ala-Pro-AFC by recombinant FAP (left) and recombinant DPP-4 (right) relative activities in the presence of the irreversible inhibitor, Ac-Gly-Pro-cmk.

The cleavage activities of FAP and DPP-4 in the presence of an irreversible dipeptide inhibitor was measured (FIGS. 9-12). In each time course study (FIGS. 9-15), the protease (FAP, DPP) and the inhibitor compound were incubated together for 4 hours, then residual activity was assayed against substrate. FIG. 9 shows a graph of relative activities of recombinant FAP and recombinant DPP-4 in cleavage of substrate L-Ala-Pro-AFC in the presence of the irreversible inhibitor Ac-Gly-Pro-cmk at different concentrations of 10, 100, and 500 µM Ac-Gly-Pro-cmk, and negative control (0 µM). cmk=chloromethyl ketone, —C(=O)CH$_2$Cl. Whereas inhibitor concentration-dependent inhibition of FAP is almost complete, DPP-4 is not inhibited by Ac-Gly-Pro-cmk. FIG. 10 shows a graph of the time course of inhibition of cleavage of substrate L-Ala-Pro-AFC by recombinant FAP (left) and recombinant DPP-4 (right) relative activities after pre-incubation with the irreversible inhibitor, Ac-Gly-Pro-cmk. Whereas FAP activity is time-dependent in the presence of inhibitor, DPP-4 is not time-dependent inhibited by Ac-Gly-Pro-cmk.

Figure 11:
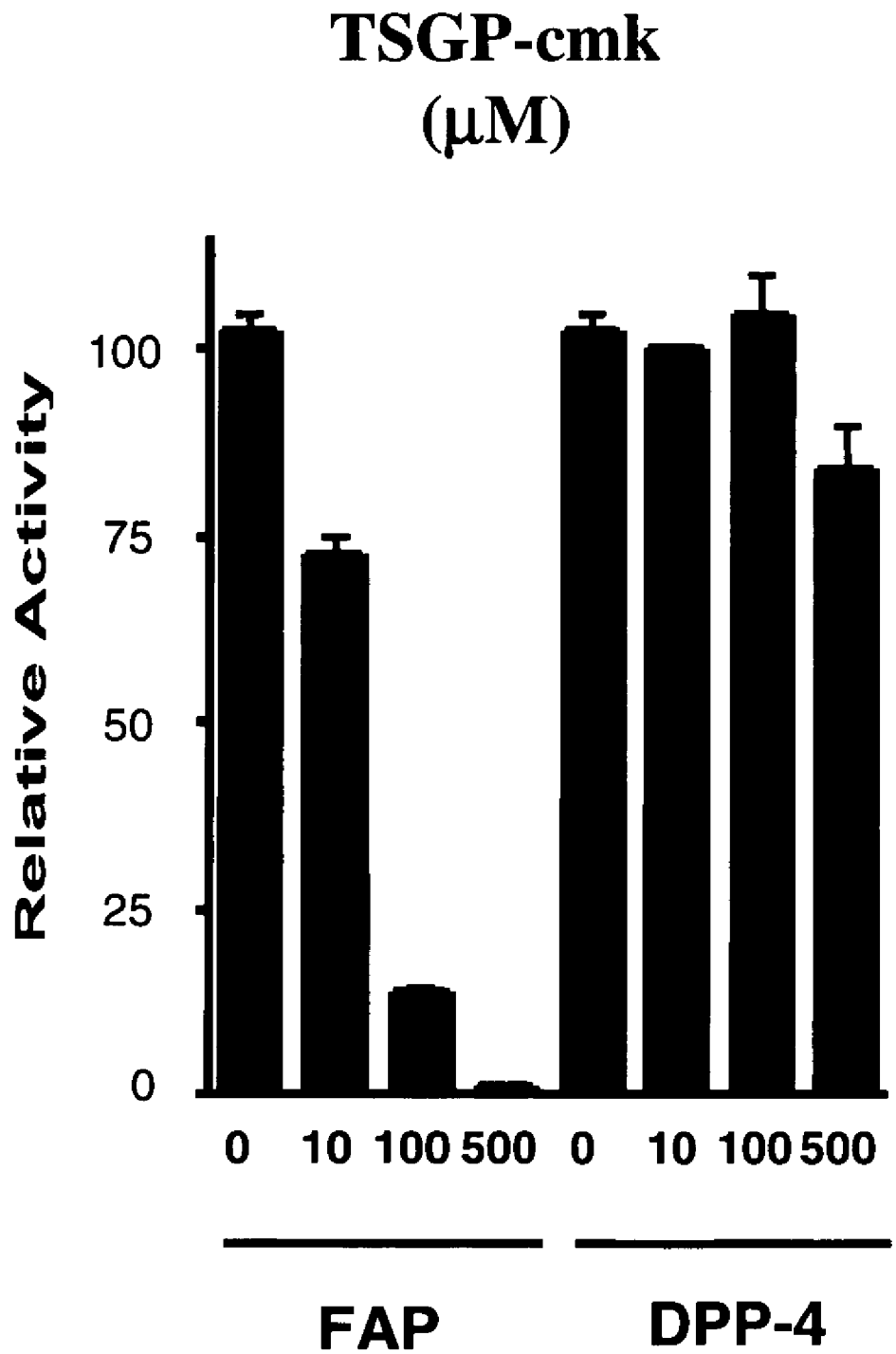
FIG. 11 shows a graph of relative activities of recombinant FAP and recombinant DPP-4 in cleavage of substrate L-Ala-Pro-AFC in the presence of the irreversible inhibitor Acetyl-Thr-Ser-Gly-Pro-cmk (TSGP-cmk) at different concentrations of 10, 100, and 500 µM Ac-Gly-Pro-cmk, and negative control (0 µM).
Figure 12:
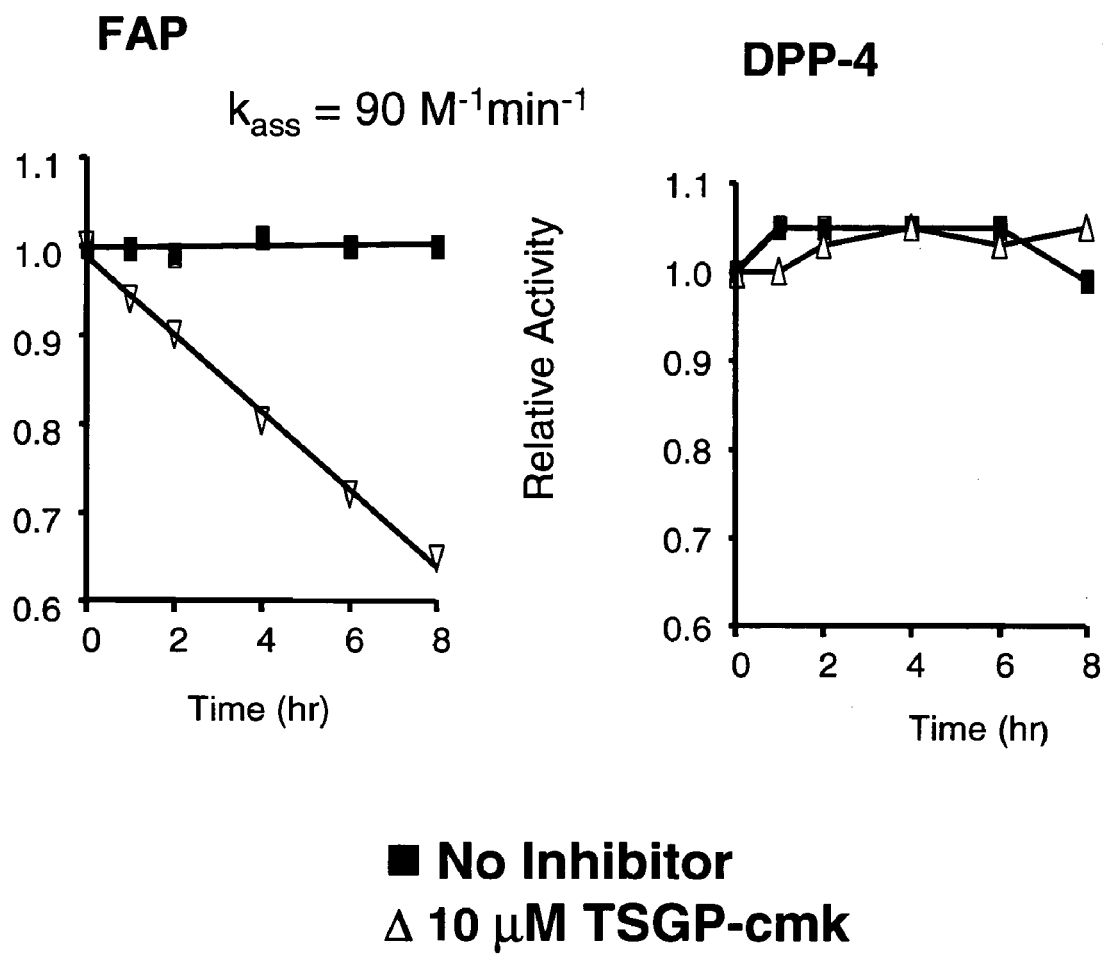
FIG. 12 shows a graph of the time course of cleavage of substrate L-Ala-Pro-AFC by recombinant FAP (left) and recombinant DPP-4 (right) relative activities in the presence of the irreversible inhibitor, TSGP-cmk.

The cleavage activities of FAP and DPP-4 in the presence of a tetrapeptide irreversible inhibitor was measured. FIG. 11 shows a graph of relative activities of recombinant FAP and recombinant DPP-4 in cleavage of substrate L-Ala-Pro-AFC in the presence of the irreversible inhibitor Acetyl-Thr-Ser-Gly-Pro-cmk (TSGP-cmk) at different concentrations of 10, 100, and 500 µM Ac-Gly-Pro-cmk, and negative control (0 µM). Whereas inhibitor concentration-dependent inhibition of FAP is almost complete, DPP-4 is not substantially inhibited by TSGP-cmk. FIG. 12 shows a graph of the time course of inhibition of cleavage of substrate L-Ala-Pro-AFC by recombinant FAP (left) and recombinant DPP-4 (right) relative activities in the presence of the irreversible inhibitor, TSGP-cmk. Whereas FAP activity is time-dependent in the presence of inhibitor, DPP-4 is not time-dependent inhibited by TSGP-cmk.

Figure 13:
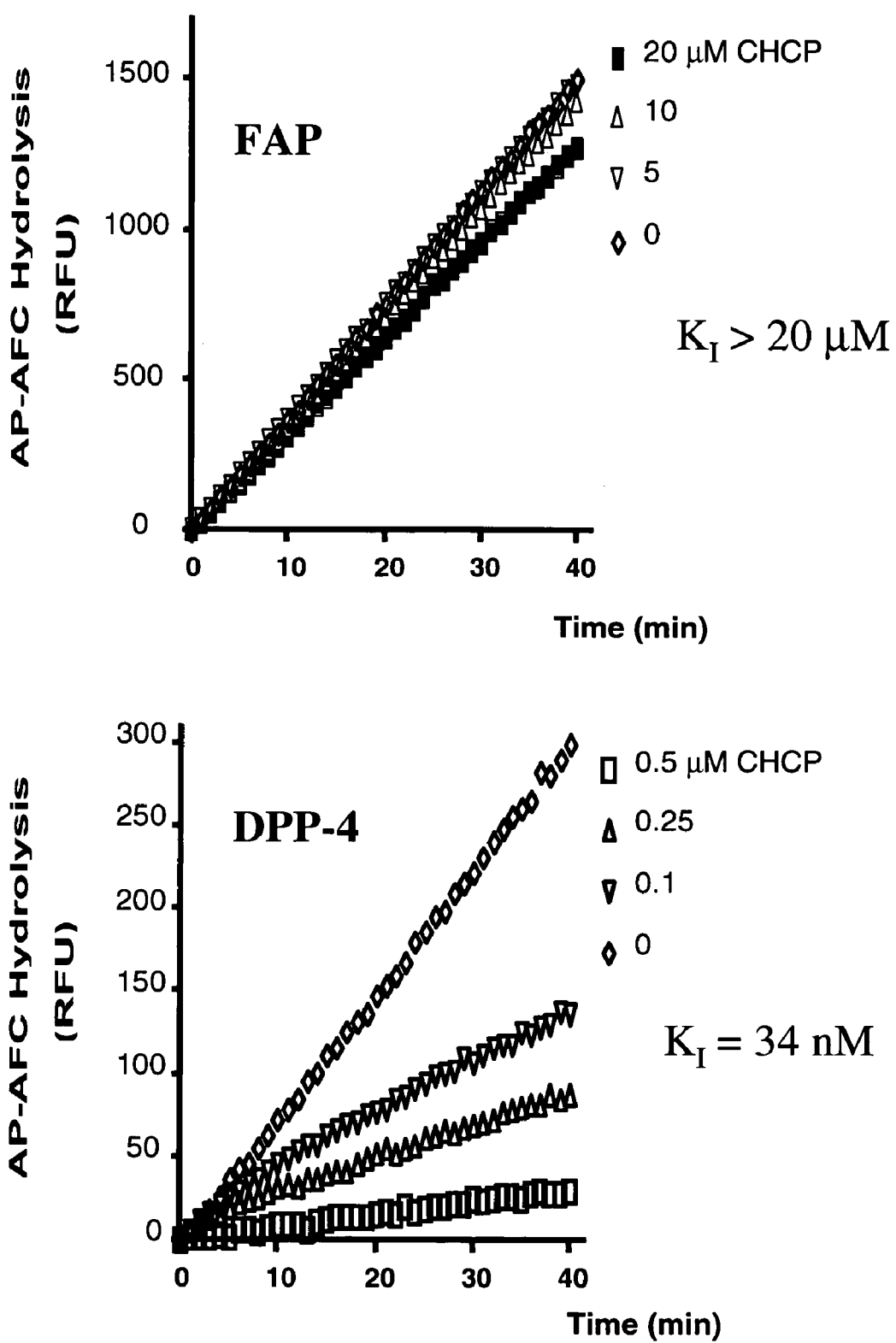
FIG. 13 shows graphs of the hydrolysis (cleavage) of the dipeptide coumarin substrate, AP-AFC by FAP (top) and DPP-4 (bottom) in the presence of different concentrations of the inhibitor, cyclohexylglycine-2-cyano-proline (CHCP), and negative control (0 µM).

FIG. 13 shows graphs of the hydrolysis (cleavage) of the dipeptide coumarin substrate, AP-AFC by FAP (top) and DPP-4 (bottom) in the presence of different concentrations of the reversible inhibitor, cyclohexylglycine-2-cyano-proline (CHCP), and negative control (0 µM). CHCP shows inhibitor concentration dependent cleavage by DPP-4, but not inhibitor concentration dependent cleavage by FAP.

FAP Inhibition Activity of N-Blocked Dipeptide Proline Boronate Compounds

Figure 14:
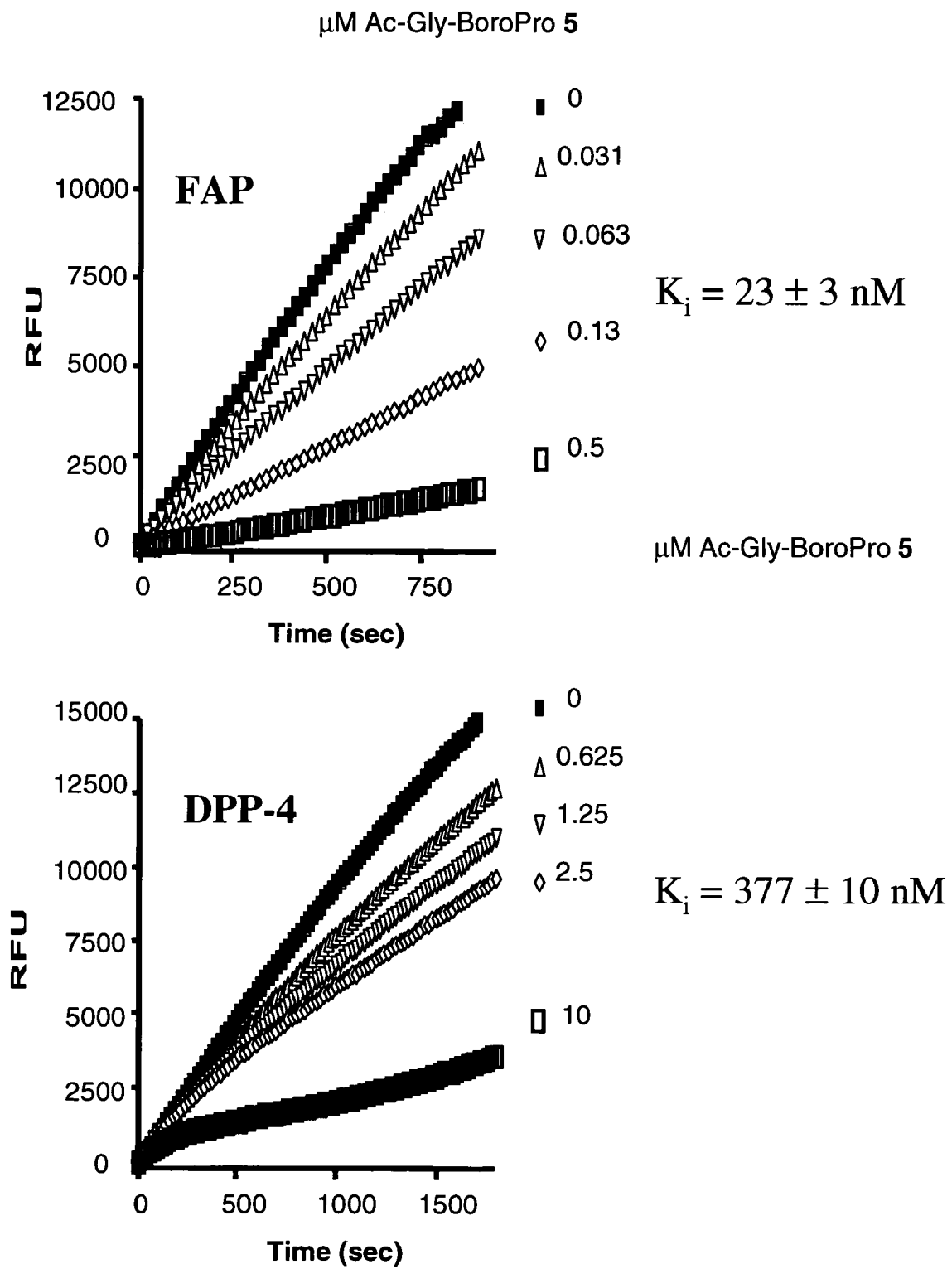
FIG. 14 shows a graph of the time course of cleavage of substrate L-Ala-Pro-AFC (5 µM) by recombinant FAP (top) and recombinant DPP-4 (bottom) measured by the release of fluorescence (RFU, relative fluorescence units) in the presence of different concentrations of FAP inhibitor, Ac-Gly-boroPro 5.

FIG. 14 shows a graph of the time course of cleavage of substrate L-Ala-Pro-AFC (5 µM) by recombinant FAP (top) and recombinant DPP-4 (bottom) measured by the release of fluorescence (RFU, relative fluorescence units) in the presence of different concentrations of FAP inhibitor, Ac-Gly-boroPro 5. FAP reacted readily with submicromolar concentrations of Ac-Gly-BoroPro, reaching steady state inhibition levels rapidly as shown in the progress curves of FIG. 14 (top). In contrast, DPP-4 required higher Ac-Gly-BoroPro concentrations for inhibition and a longer time to reach steady state inhibition levels (FIG. 14 bottom). The steady states of product formation in the absence ($V_0$) and presence of inhibitor ($V_i$) were used to calculate apparent inhibition constants ($K_{iapp}$) by plotting $V_0/V_i-1$ against inhibitor concentration. The calculated inhibition constants ($K_i$) were 23±3 nM for FAP and 377±18 nM for DPP-4 (Table 9), indicating that the Ac-Gly-Pro motif provides ~16-fold selectivity for FAP inhibition.

The $K_i$ values and selectivity of several other N-terminal blocked Gly-boroPro inhibitors of cleavage of substrate L-Ala-Pto-AFC by FAP, DPP-4, and POP are shown in Table 8:

TABLE 8

Inhibition of FAP and DPP-4 by N-blocked Gly-boroPro compounds

| Inhibitor | FAP $K_i$ (nM) | DPP-4 $K_i$ (nM) | FAP/DPP-4 Selectivity | POP $K_i$ (nM) |
|---|---|---|---|---|
| N-Ac-Gly-boroPro 5 | 23 | 377 | 16.4 | 211 |
| N-Ac-(D)Ala-boroPro | 655 | >40,000 | >60 | |
| N-isobutyryl-Gly-boroPro | 51 | 4300 | 84 | |
| N-benzoyl-Gly-boroPro | 142 | >10,000 | >70 | |
| N-benzoyl-Sarcosyl-boroPro | 191 | >50,000 | >262 | 48 |
| N-isobutyryl-sarcosyl-boroPro | 265 | 19,500 | 74 | 63 |
| N-benzyl-Gly-boroPro | 48 | 56 | 1.2 | |
| N-(2,6-dimethylbenzoyl)-Gly-boroPro | 25 | 1100 | 44 | |
| N-(2,6-dichlorobenzoyl)-Gly-boroPro | 29 | 9500 | | 2.2 |
| N-pivaloyl-Gly-boroPro | 11,900 | ND | ND | |
| N-mesyl (CH$_3$SO$_2$)-Gly-boroPro | 246 | 1430 | 5.8 | |
| N-Ac-Ser-Gly-boroPro | 16,500 | >40,000 | >3 | |

The N-mesylated Gly-boroPro compound is active against FAP, but less selective than Ac-Gly-boroPro 5. The N-blocked tripeptide, Ac-Ser-Gly-boroPro, was not as active or selective as 5.

Figure 15:
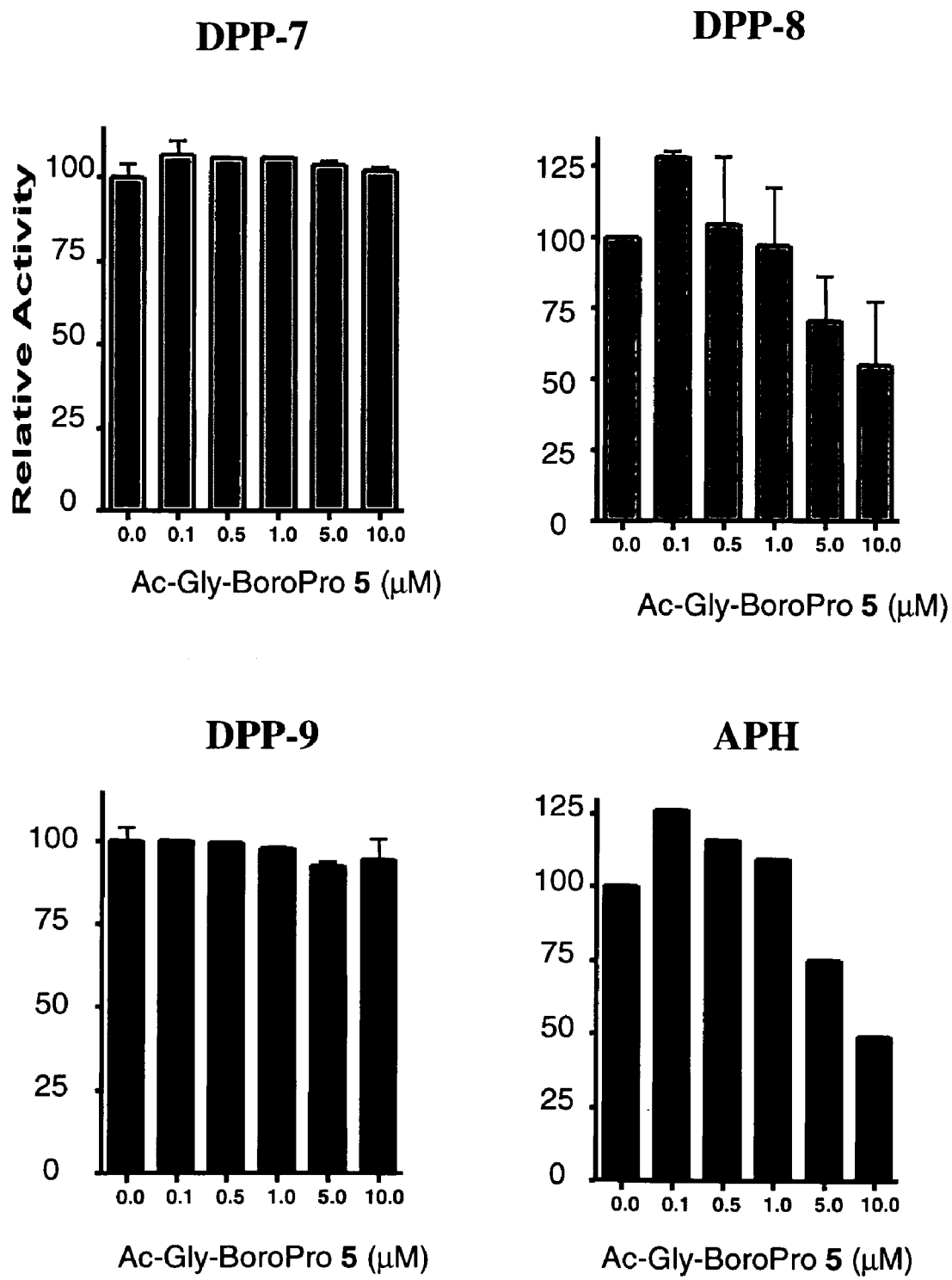
FIG. 15 shows a graph of the time course of cleavage of substrate L-Ala-Pro-AFC by dipeptidyl peptidases, DPP-7 (upper left), DPP-8 (upper right), DPP-9 (lower left), and APH, acetylpeptide hydrolase (lower right) measured by the release of fluorescence to measure relative enzymatic activity, in the presence of different concentrations, 5.0, 1.0, 0.5, 0.1 µM, and negative control (0 µM), of FAP inhibitor, Ac-Gly-boroPro.

FIG. 15 shows graphs of protease inhibition dose response in cleavage of substrate L-Ala-Pro-AFC by dipeptidyl peptidases, DPP-7 (upper left), DPP-8 (upper right), DPP-9 (lower left), and APH, acetylpeptide hydrolase (lower right) measured by the release of fluorescence to measure residual relative enzymatic activity, in the presence of different concentrations, 5.0, 1.0, 0.5, 0.1 µM, and negative control (0 µM), of FAP inhibitor, Ac-Gly-boroPro 5. Many of these proteases show ubiquitous distribution (Rosenblum, J. S. and Kozarich, J. W. (2003) Current Opinion in Chemical Biology 7:496-504). To establish whether Ac-Gly-BoroPro 5 inhibits these prolyl peptidases, each protease was cloned, expressed and assayed to determine $K_m$ and $K_i$ values and monitor their activity. Strikingly, Ac-Gly-BoroPro 5 inhibited these prolyl peptidases with $K_i$ values ranging from ~9- to ~5400-fold higher than that for FAP inhibition, indicating that the Ac-Gly-Pro motif confers significant FAP selectivity. The inhibitor 5 has only limited activity against these dipeptidyl peptidases and is a selective inhibitor of FAP (Table 9). Compound 5 inhibits full-length (transmembrane) murine FAP at 117 nM in cell lysate.

TABLE 9

Inhibition of selected proteases by N-acetyl-gly-boroproline 5. Selectivity is normalized to FAP

| Protease | $K_I$ (nM) | Selectivity |
|---|---|---|
| FAP | 23 | 1 |
| DPP-4 | 377 | 16.4 |
| DPP-8 | 19,100 | 830 |
| DPP-9 | 8800 | 383 |
| APH | 575 | 25 |
| POP | 211 | 9.2 |
| DPP-7 | 125,000 | 5434 |
| PCP | ND | ND |

The data presented herein defines FAP as a dual activity protease, having both dipeptidase and Gly-Pro-cleaving endopeptidase activity. This substrate specificity distinguishes FAP from other prolyl peptidases that act as single activity proteases, including DPPs-4, -7, -8, and -9, which act solely as dipeptidases (Mentlein, R. (1999) Regulatory Peptides 85:9-24; Augustyns, et al (2005) Current Medicinal Chemistry 12:971-998; Underwood, et al (1999) J. Biol. Chem 274(48):34053-34058; Abbott, et al (2000) Eur. J. Biochem. 267:6140-6150; Ajami, et al (2004) Biochemica et Biophysica Acta 1679:18-28) and POP, which displays only endopeptidase activity (Polgar, L. (2002) Cellular and Molecular Life Sciences 59, 349-362). Additionally, the dual activity of FAP is distinct from APH (Jones, et al (1991) Proc. Natl. Acad. Sci. USA 88, 2194-2198) and PCP (Odya, et al (1978) J. Biol. Chem 253(17), 5927-5931), which lack both dipeptidase and endopeptidase activity. APH acts as an N-acetyl amino acid hydrolase and PCP acts as a Pro-X carboxypeptidase. Thus, the unique substrate specificity of FAP is distinct from other prolyl peptidases and offers possibilities for selective inhibitor design.

Based on the unique reactivity of FAP with N-acyl-Gly-Pro-based substrates, we developed amino terminus-blocked peptide proline boronate compounds of Formulas I and II. An embodiment of Formula I, Ac-Gly-BoroPro 5, selectively inhibited FAP relative to other prolyl peptidases. This selectivity profile and the N-acyl-linkage in Ac-Gly-BoroPro 5 differentiate it from other boronic acid inhibitors targeting prolyl peptidases, including: Val-BoroPro compounds (Flentke et al (1991) Proc. Natl. Acad. Sci. USA 88:1556-1559; Coutts et al (1996) J. Med. Chem. 39:2087-2094; Snow et al (1994) J. Amer. Chem. Soc. 116(24): 10860-10869; Shreder et al. (2005) Bioorganic and Medicinal Chemistry Letters 15:4256-4260); N-alkyl-Gly-BoroPro compounds (Hu, et al (2005) Bioorganic and Medicinal Chemistry Letters 15:4239-4242); and Boro-norleucine compounds (Shreder et al (2005) Bioorganic and Medicinal Chemistry Letters 15:4256-4260). Val-BoroPro and N-alkyl-Gly-BoroPro inhibitors target most prolyl peptidases, whereas Boro-norleucine-based inhibitors selectively target DPP-7. Additionally, these inhibitors contain a free amine at their N-terminus, which allows intra-molecular reaction with the electrophilic boron, resulting in cyclization and inhibitor inactivation. In contrast, the N-blocked feature in amino terminus-blocked peptide proline boronate compounds blocks the N-terminus of the inhibitor, making it less nucleophilic and therefore unlikely to cyclize. Ac-Gly-BoroPro shows poor reactivity with DPP-8 and DPP-9. Selective inhibition of DPP-8 and DPP-9 causes severe toxicity in animals (Lankas et al (2005) Diabetes 54:2988-2994).

The compounds of the invention, Formulas I and II, may be assayed for prolyl peptidase (POP) inhibition by the methods described herein, as well as by those described by Venalainen et al (2006) Biochemical Pharmacology 71:783-692.

Administration of N-Blocked Peptide Proline Boronate Compounds

The N-blocked dipeptide proline boronate compounds of the invention, Formulas I and II, may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary, and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the N-acylated dipeptide proline boronate compound is administered orally, it may be formulated as a pill, capsule, tablet, etc. with a pharmaceutically acceptable carrier or excipient. Where the N-acylated dipeptide proline boronate compound is administered parenterally, it may be formulated with a pharmaceutically acceptable parenteral vehicle and in a unit dosage injectable form, as detailed below.

Pharmaceutical Formulations of N-Acylated Dipeptide Proline Boronate Compounds

Compounds of the present invention are useful for treating diseases, conditions and/or disorders modulated by FAP. Therefore, an embodiment of the present invention is a pharmaceutical composition, i.e. formulation, comprising a therapeutically effective amount of a compound of the present invention and a pharmaceutically acceptable excipient, diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, a kit or article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical, formulations of therapeutic N-acylated dipeptide proline boronate compounds of the invention may be prepared for various routes and types of administration. An N-acylated dipeptide proline boronate compound having the desired degree of purity is optionally mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The inhibitory compound for use herein is preferably sterile. The compound ordinarily will be stored as a solid composition, although lyophilized formulations or aqueous solutions are acceptable.

The pharmaceutical compositions of the invention will be formulated, dosed, and administered in a fashion, i.e. amounts, concentrations, schedules, course, vehicles, and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients, and stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the N-acylated dipeptide proline boronate compound, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile, which is readily accomplished by filtration through sterile filtration membranes.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of N-acylated dipeptide proline boronate compound suitable for oral administration may be prepared as discrete units such as pills, capsules, cachets or tablets each containing a predetermined amount of the N-acylated dipeptide proline boronate compound.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g. gelatin capsules, syrups or elixirs may be prepared for oral use. Formulations of a N-acylated dipeptide proline boronate compound intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. Excipients may include, but are not limited to, calcium carbonate, sodium carbonate, lactose, calcium phosphate, sodium phosphate, mannitol, crospovidone, polysorbate 80, hydroxypropyl methylcellulose, colloidal silicon dioxide, microcrystalline cellulose, sodium starch glycolate, simethicone, polyethylene glycol 6000, sucrose, magnesium carbonate, titanium dioxide, methylparaben, and polyvinyl alcohol. Excipients may also include granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For infections of the eye or other external tissues e.g. mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of the invention contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical composition of a N-acylated dipeptide proline boronate compound may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of HIV infections as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example pills, sealed ampoules, vials, and blister packs. Formulations may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

An N-blocked dipeptide proline boronate compound of the invention may be combined in a pharmaceutical combination formulation, or dosing regimen as combination therapy, with a second compound that has anti-hyperproliferative properties or that is useful for treating a hyperproliferative disorder (e.g. cancer). The second compound of the pharmaceutical combination formulation or dosing regimen preferably has complementary activities to the N-acylated dipeptide proline boronate compound of the combination such that they do not adversely affect each other. Such molecules are suitably present in combination in amounts that are effective for the purpose intended.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

Metabolites of N-Acylated Dipeptide Proline Boronate Compounds

Also falling within the scope of this invention are the in vivo metabolic products of the N-acylated dipeptide proline boronate compounds described herein, to the extent such products are novel and unobvious over the prior art. Such products may result for example from the oxidation, reduction, hydrolysis, amidation, deamidation, esterification, deesterification, enzymatic cleavage, and the like, of the administered compound. Accordingly, the invention includes novel and unobvious compounds produced by a process comprising contacting a compound of this invention with a mammal for a period of time sufficient to yield a metabolic product thereof.

Metabolite products typically are identified by preparing a radiolabelled (e.g. $^{14}C$ or $^{3}H$) isotope of a compound of the invention, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS, LC/MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the N-acylated dipeptide proline boronate compounds of the invention.

Articles of Manufacture

In another embodiment of the invention, an article of manufacture, or "kit", containing materials useful for the treatment of the disorders described above is provided. The article of manufacture comprises a container and a label or package insert on or associated with the container. Suitable containers include, for example, bottles, vials, syringes, blister pack, etc. The containers may be formed from a variety of materials such as glass or plastic. The container holds a N-acylated dipeptide proline boronate compound or formulation thereof which is effective for treating the condition and may have a sterile access port (for example the container may be an intravenous solution bag or a vial having a stopper pierceable by a hypodermic injection needle). At least one active agent in the composition is an N-acylated dipeptide proline boronate compound of the invention. The label or package insert indicates that the composition is used for treating the condition of choice, such as cancer. In one embodiment, the label or package insert includes instructions for use and indicates that the composition comprising the N-acylated dipeptide proline boronate compound can be used to treat a hyperproliferative disorder.

The article of manufacture may comprise (a) a first container with a N-acylated dipeptide proline boronate compound of Formula I or II contained therein; and (b) a second container with a second pharmaceutical formulation contained therein, wherein the second pharmaceutical formulation comprises a second compound with anti-hyperproliferative activity. The article of manufacture in this embodiment of the invention may further comprise a package insert indicating that the first and second compounds can be used to treat patients a hyperproliferative disorder, such as cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXAMPLES

Materials—Ala-Pro-7-amino-4-trifluoromethylcoumarin (AFC), Phe-Pro-AFC, Gly-Pro-AFC, Ile-Pro-AFC, Acetyl (Ac)-Gly-Pro-AFC and Lys-Ala-AFC were from Enzyme Systems Products, Livermore Calif. Benzyloxycarbonyl (Z)-Gly-Pro-7-amino-4-methylcoumarin (AMC), Gly-Ala-AMC, Ac-Ala-AMC and amino acid derivatives were from Bachem California Inc., Torrance Calif. An Ac-$P_2$-$Pro_1$-AFC substrate library, where $P_2$ was varied with all amino acids (except Cys and Trp), was custom synthesized by Enzyme Systems Products. N-substituted-Gly-Pro-7-amino-4-methyl-3-carbamoylcoumarin (AMCC) substrates and a $P_2$-$Pro_1$-AMCC substrate library were prepared essentially as described in Maly, et al (2002) J. Org. Chem. 67:910-915 with the exception that 7-amino-4-methyl-3-coumarinylacetic acid was used as the labelling fluorophore reagent (available from Fluka Chemicals, Sigma-Aldrich Co. as AMCA-H, 08445 [106562-32-7]; MW=233.22). 7-Amino-4-methyl-3-coumarinylacetic acid was attached to an amine-producing peptide synthesis resin so that after coupling of amino acids and cleavage from the resin, the acetamide moiety was produced at the carboxyl terminus of the $P_2$-$Pro_1$-AMCC substrates. N-acetylated substrates were prepared by treating peptides on resin with acetic anhydride in 10% triethylamine/dichloromethane until the resin was negative to the Kaiser ninhydrin test (Sarin, et al (1981) Anal. Biochem. 117(1):147-157). Formylated substrates were prepared as described in Fields, et al (1988) Proc. Natl. Acad. Sci. USA 85(5):1384-1388. Ac-Gly-Proline boronic acid (BoroPro) was synthesized as described in Gibson, et al (2002) Org. Proc. Res. Dev. 6(6):814-816, except that Ac-Gly was substituted for Val, making deprotection unnecessary. Substrates and inhibitors were purified by reverse phase chromatography and verified by matrix assisted laser-desorption ionization mass spectrometry. N-Glycanase was from Sigma-Aldrich Co., St. Louis, Mo.

Example 1

FAP Expression and Purification

Protease Cloning and Expression—cDNAs encoding the extra-cellular domains (ECDs) of DPP-4 (amino acids 39-766) and FAP (amino acids 38-760) were generated by polymerase chain reaction (PCR) using Quick Clone cDNA library (Stratagene, La Jolla, Calif.) as a template with forward and reverse primers:

```
FAP.fwd
5'ATGCGGCCGCGACAATGAGAGCACTCACACTG3'    SEQ ID NO.1

FAP.rev
5'ACGGATCCTTAGTCTGACAAAGAGAAAC3'        SEQ ID NO.2

DPP-4.fwd
5'ATGCGGCCGCGAGTCGCAAAACTTACACTCTAAC3'  SEQ ID NO.3

DPP-4.rev
5'-GCGGATCCCTAAGGTAAAGAGAAACATTG3'      SEQ ID NO.4
```

PCR products were TA-cloned into pGemT (Promega) and confirmed by DNA sequencing. Confirmed cDNAs were then sub-cloned into pFLAG-CMV1 (Sigma-Aldrich, St. Louis Mo.) for expression as N-terminally FLAG-tagged proteins. Plasmids containing full-length DPP-7, DPP-8, DPP-9, POP, and APH were obtained from Origene and used as templates to generate pFLAG-CMV1 expression constructs encoding each protease as above. These constructs encoded amino acids 26-492 of DPP-7, 2-883 of DPP-8, 2-864 of DPP-9, 2-710 of POP and 2-732 of APH.

For protein production, 293 cells were transfected with plasmids encoding FAP-ECD or DPP-4-ECD using calcium phosphate and purified proteins from serum-free conditioned media by affinity chromatography with M2 anti-FLAG resin (Sigma) or NTA-Nickel resin (Qiagen Co., Valencia Calif.). Proteins were >95% pure as determined by sodium dodecyl sulfate (SDS)-polyacrylamide gel electrophoresis (PAGE) with coomassie blue staining, with the exception of DPP8, which had a purity of ~70%. Protein concentrations were determined by the bichinconic acid (BCA) method (BioRad Laboratories, Hercules, Calif.). Typical yields were 1 mg/liter for FAP and 2.5 mg/l for DPP-4.

FAP-expressing cell lines, such as HT 1080 fibrosarcoma cells or human embryonic kidney 293 cells, may be prepared for example, by transfection following Examples 9 and 10 of US 2003/0055052 or Park et al (1999) J. Biol. Chem. 36505-36512, and assayed for FAP expression in an immunofluorescence assay using the FAP-specific mAb F19 (Garin-Chesa et al (1990) Proc. Natl. Acad. Sci USA 87(18):7235-7239). Soluble recombinant FAP may be prepared following Example 11 of US 2003/0055052. FAP may also be produced in insect cells as a hexa-His-tagged protein using a recombinant baculovirus expression system. Two isoforms of FAP, glycosylated and nonglycosylated, were identified by Western blotting using an anti-His-tag antibody and separated by lectin chromatography. The glycosylated FAP was purified to near homogeneity using immobilized metal affinity chromatography (Sun et al (2002) Protein Expression and Purification 24(2):274-281). FAP and other proteases were expressed with an N-terminal FLAG tag and purified on anti-FLAG antibody M2 affinity gel (Sigma Aldrich, St. Louis Mo.).

Gel Filtration Chromatography and Light Scattering Analysis

To calculate the stoichiometry of purified protease preparations, the molecular weight of each protease was measured using multi-angle light scattering in combination with gel filtration chromatography and interferometric refractometry. This method allows accurate determination of a protein's molecular weight based on protein concentration, refractive index and the degree of light scattering. Proteases (50 µg) in tris buffered saline (TBS; 50 mM Tris (pH 7.4), 100 mM NaCl) were loaded onto a Shodex KW-803 gel filtration column (Flow rate 0.5 ml/min) coupled to an Agilent 1100 FPLC equipped with a DAWN EOS 18-angle light scattering detector (Wyatt Technology, Santa Barbara Calif.) and an OPTI-LAB DSP interferometric refractometer (Wyatt Technology). ASTRA software was used for molecular mass calculations.

Example 2

In Vitro Assay of FAP Activity

Protease Assays—Protease activity was monitored continuously using a SpectraMax M2 microplate reader (Molecular Devices Corp., Sunnyvale Calif.) in the kinetic mode. Assays were conducted at 23° C. in 50 mM Tris (pH 7.4), 100 mM NaCl, 1 mM EDTA. The excitation/emission wavelengths for the different fluorogenic substrates were 360/460 nm (AMC), 400/505 nm (AFC), 340/425 nm (MNA), 340/

510 nm (EDANS), and 337/425 nm (Abs). Standard curves of the appropriate fluorescent product versus concentration were used to convert relative fluorescence units to nmol of product produced. Substrates in the X-Pro-AMC library were used in rate assays at 5 µM final concentration. Generally, kinetic constants ($k_{cat}$, $K_m$) were determined with initial rate ($V_0$) measurements, using substrate concentrations in the range of 0.1-5 $K_m$ value and protease concentrations of 10-35 nM. The kinetic parameters were calculated from Michaelis-Menten plots ($V_0$ versus [S]) with nonlinear regression analysis using GraphPad software. $k_{cat}$ values were calculated under the assumption that each protease was 100% active.

When saturating amounts of substrate could not be achieved, catalytic efficiencies ($k_{cat}/K_m$) were determined under pseudo-first order conditions ([S]<<the estimated $K_m$) and fit to the following equation: $Ln[S_t/S_0]=-k_{obs}t$, where $S_t$ is the concentration of substrate remaining at time t, $S_0$ is the initial substrate concentration and $k_{obs}$ is the apparent first order substrate cleavage constant equal to ($k_{cat}/K_m$) times $E_T$, the total enzyme concentration (Copeland, R. (2000) Enzymes, A Practical Introduction to Structure, Mechanism, and Data Analysis, 2nd Ed., John Wiley and Sons, Inc, New York). The linear relationship of $Ln[S_t/S_0]$ versus time allows calculation of $k_{cat}/K_m$ by dividing the slope of the plot by $E_T$.

Inhibition Kinetics—$K_I$ values for inhibition of proteases by Ac-Gly-BoroPro were determined using the method of progress curves for analysis of tight-binding competitive inhibitors (Henderson, P. J. (1972) Biochem J. 127:321-333). Briefly, proteases were added to a reaction mixture containing inhibitor and substrate (Ac-Ala-AMC for APH, Z-Gly-Pro-AMC for POP, and Ala-Pro-AFC for all others) in assay buffer at 23° C. Protease activity was followed continuously as described above to monitor time-dependent inhibition. Data were plotted as $V_0/V_i-1$ versus [I], where $V_0$ is the rate if substrate hydrolysis in the absence of inhibitor, $V_i$ is the steady state rate of substrate hydrolysis in the presence of inhibitor and [I] is the concentration of Ac-Gly-BoroPro. Plots of $V_0/V_i-1$ versus [I] were linear and the apparent inhibition constant, $K_{app}$, was determined from the reciprocal of the slope. $K_i$, the true equilibrium inhibition constant was determined according to the following relationship: $K_i=K_{app}/(1+[S]/K_m)$, where [S] is the concentration of substrate used in the assay and $K_m$ is the Michaelis constant for substrate cleavage (Edosada et al (2006) Jour. Biological Chem. 281 (11):7437-7444 at page 7438).

Inhibition Assays with Ac-GP-cmk and Ac-TSGP-cmk

Acetyl-gly-pro-chloromethyl ketone and acetyl-thre-ser-gly-pro-cmk were custom synthesized at Anaspec (San Jose, Calif.). Recombinant FAP (160 nM) and DPP-4 (160 nM) were reacted with Ac-GP-cmk or TSGP-cmk (0-500 µM) at 37° C. in 50 mM Tris-HCl, pH 7.5 containing 100 mM NaCl, and 0.1 mg/ml bovine serum albumin (assay buffer). After 6 hours, residual protease activity against AP-AFC (50 µM) was measured using a Molecular Devices M2 plate reader in the kinetic mode (excitation 400 nM, emission 505 nM). Inhibition data are graphed as residual activity relative to protease activity in the absence of inhibitor.

Inhibition of FAP and DPP-4 by the cmk-based inhibitors was studied under pseudo-first order conditions. Proteases (100 nM) were reacted with 10 µM inhibitor in assay buffer at 37° C. for increasing amounts of time. Residual protease activity was then measured using AP-AFC (50 µM) as a substrate. Pseudo-first order rate constants were calculated from the slope of plots of Ln (residual protease activity) versus time. Apparent association constants ($k_{ass}$) for inhibition were determined from the relationship $k_{ass}=k_{obs}/[I]$, where $k_{obs}$ is the pseudo-first order rate constant and [I] is the inhibitor concentration.

Example 3

Inhibition of Cell Surface FAP

Bone marrow HS5 stromal cells express cell surface FAP and DPP-4 as determined by FACS (fluorescent activated cell sorting). These cells were treated with DMSO vehicle or Ac-GP-cmk (100 µM) twice a day for a total of three doses. Cells were then lysed in 1 ml lysis buffer (50 mM Tris, pH 7.5 containing 100 mM NaCl and 1% v/v triton X-100) and cellular debris pelleted by centrifugation (10,000 g for 10 min). Lysate supernatants (350 µg) were incubated with 2 µg anti-FAP (generated in house) or anti-DPP-4 (clone M-A261; Pharmingen) overnight at 4° C. Immune complexes were then recovered with 50 µl protein A/G beads (Pierce Biotechnology Inc., Rockford Ill.). After washing, protease activity against AP-AFC (250 µM) was measured.

Example 4

Protease Inhibition by Ac-Gly BoroPro 5

$K_I$ values for inhibition of proteases by 5 were determined using the method of progress curves. Briefly, proteases (10-100 nM) were added to a reaction mixture containing inhibitor 5 (0-10 µM) and substrate AP-AFC in assay buffer at 23° C. Protease activity was monitored by following release of AFC (Excitation 400 nm/Emission 505 nm) with time using a Molecular Devices M2 plate reader. Data were plotted as $V_0/V_i-1$ versus [I], where $V_0$ is the rate if substrate hydrolysis in the absence of inhibitor, $V_i$ is the steady state rate of substrate hydrolysis in the presence of inhibitor and [I] is the concentration of 5. Plots of $V_0V_i-1$ versus [I] were linear and the observed inhibition constant, $K_{obs}$, was determined from the reciprocal of the slope. $K_i$, the true equilibrium inhibition constant was determined according to the following relationship: $K_i=K_{obs}/(1+[S]/K_m)$, where [S] is the concentration of substrate used in the assay and $K_m$ is the Michaelis constant for substrate cleavage.

Plasmids encoding full-length proteases were obtained from Origene Technologies Inc., Rockville Md. Proteases DPP-7, DPP-8, DPP-9, POP, PCP and APH were amplified by PCR and subcloned into pFLAG-CMV1 for expression as soluble molecules. PFLAG-CMV 1 plasmids containing the appropriate protease constructs were transfected into 293 cells via the calcium phosphate method. 72 hours after transfection, proteases were purified from culture supernatants using M2 anti-FLAG resin (Sigma-Aldrich Co., St. Louis Mo.). After extensive washing, proteases were eluted off the resin with 0.1 M glycine pH 2.5 and immediately neutralized with 1 M Tris, pH 8.0. Following concentration and dialysis into the appropriate assay buffer, proteases were used for in vitro kinetic analyses.

Example 5

Synthesis of FRET Labelled Peptides

A general protocol for conjugating the dyes in the NHS ester form to peptides entails dissolving the NHS esters in aqueous acetonitrile (the percentage of acetonitrile is determined by the hydrophobicity of the dye to attain solubility) with peptides in water (or aqueous acetonitrile solution if peptides were hydrophobic). Aqueous sodium bicarbonate buffer (1 M) is added to the solution to achieve 0.1 M buffer concentration while vortexing or shaking. The mixture is shaken at room temperature for 10 minutes to 30 minutes. The crude peptide-dye conjugate in the reaction mixture can be directly purified by reverse-phase HPLC.

N-acetyl-gly-boroproline 4. Borate exchange of 4 with phenylboronic acid in MTBE and water gave N-acetyl-gly-boroproline 5.

Example 6

Synthesis of N-Acetyl-Gly-Boroproline 5

N-acetyl-gly-boroproline 5 was prepared according to the synthetic route of FIG. 1. Metallation of tert-butyl 1-pyrrolidinecarboxylate (N-t-BOC-pyrrolidine, Sigma-Aldrich Co.) in THF with sec-butyllithium, followed by addition of trimethylborate gave 1-(tert-butoxycarbonyl)pyrrolidin-2-yl-2-boronic acid 1 after quenching with aqueous NaOH and extraction. Borate esterification with the (1S, 2S, 3R, 5S), (+)-pinanediol in methyl, tert-butyl ether (MTBE) gave borate ester 2. Acid hydrolysis of the BOC protecting group and selective crystallization in isopropyl alcohol gave (+)-pinane 1-pyrrolidin-2-yl-2-boronate 3. Coupling of 3 and N-acetyl glycine with EDC (N-ethyl-N'-(3-dimethylaminopropyl)carbodiimide), HOBt (1-hydroxybenzotriazole), and DiPEA (diisopropylethylamine gave the pinane borate of

We claim:
1. A compound of Formula Ib:

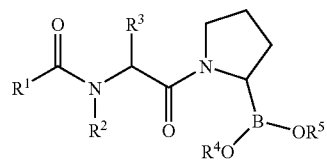

Ib or stereoisomer, tautomer, or pharmaceutically acceptable salt thereof, wherein:

$R^1$ is selected from hydrogen, methyl, isobutyl, tert-butyl, cyclohexyl, cyclopentyl, phenyl and phenyl substituted with one to three substituents selected from the group consisting on methyl, ethyl and propyl;

$R^2$ is selected from H and $C_1$-$C_8$ alkyl;

$R^3$ is selected from hydrogen, methyl, isopropyl, n-propyl, isobutyl, sec-butyl, n-butyl, —$CH_2OH$ and —CH(OH)$CH_3$, $R^4$ and $R^5$ are independently selected from H and $C_1$-$C_8$ alkyl;
each alkyl is optionally and independently substituted with one or more substituents selected from F, Cl, Br, I, OH, OR, R, =O, =S, =NR, =N$^+$(O)(R), =N(OR), =N$^+$(O)(OR), =N-N(R)$_2$, —C(=Y)R, —C(=Y)OR, —C(=Y)N(R)$_2$, —N(R)$_2$, —N$^+$(R)$_3$, —N(R)C(=Y)R, —N(R)C(=Y)OR, —N(R)C(=Y)N(R)$_2$, —SR, —OC(=Y)R, —OC(=Y)OR, —OC(=Y)(N(R)$_2$), —OS(O)$_2$(OR), —OP(=Y)(OR)$_2$, —OP(OR)$_2$, —P(=Y)(OR)$_2$, —P(=Y)(OR)NR$_2$, —S(O)R, —S(O)$_2$ R, —S(O)$_2$NR, —S(O)(OR), —S(O)$_2$(OR), —SC(=Y)R, —SC(=Y)OR, and —SC(=Y)NR$_2$;
R is independently H, $C_1$-$C_8$ alkyl, $C_2$-$C_8$ alkenyl, $C_2$-$C_8$ alkynyl, $C_6$-$C_{20}$ aryl, $C_1$-$C_{20}$ heterocyclyl, or a protecting group selected from a trialkylsilyl, a dialkylphenylsilyl, benzoate, benzyl, benzyloxymethyl, methyl, methoxymethyl, a triarylmethyl, phthalimido and tetrahydropyranyl; and
Y is independently O, S, NR, N$^+$(O)(R), N(OR), N$^+$(O)(OR), or N-N(R)$_2$.

2. A compound of formula:

or stereoisomer, tautomer, or pharmaceutically acceptable salt thereof, wherein:
Z is $R^1$ is selected from hydrogen, methyl, isobutyl, tert-butyl, cyclohexyl, cyclopentyl, phenyl and phenyl substituted with one to three substituents selected from the group consisting on methyl, ethyl and propyl;
each $R^2$ is selected from H and $C_1$-$C_8$ alkyl;
$R^3$ is selected from hydrogen, methyl, isopropyl, n-propyl, isobutyl, sec-butyl, n-butyl, —CH$_2$OH and —CH(OH)CH$_3$;
$R^4$ and $R^5$ are independently selected from H and $C_1$-$C_8$ alkyl;
each alkyl is optionally and independently substituted with one or more substituents selected from F, Cl, Br, I, OH, OR, R, =O, =S, =NR, =N$^+$(O)(R), =N(OR), =N$^+$(O)(OR), =N-N(R)$_2$, —C(=Y)R, —C(=Y)OR, —C(=Y)N(R)$_2$, —N(R)$_2$, —N$^+$(R)$_3$, —N(R)C(=Y)R, —N(R)C(=Y)OR, —N(R)C(=Y)N(R)$_2$, —SR, —OC(=Y)R, —OC(=Y)OR, —OC(=Y)(N(R)$_2$), —OS(O)$_2$(OR), —OP(=Y)(OR)$_2$, —OP(OR)$_2$, —P(=Y)(OR)$_2$, —P(=Y)(OR)NR$_2$, —S(O)R, —S(O)$_2$ R, —S(O)$_2$NR, —S(O)(OR), —S(O)$_2$(OR), —SC(=Y)R, —SC(=Y)OR, and —SC(=Y)NR$_2$;
R is independently H, $C_1$-$C_8$ alkyl, $C_2$-$C_8$ alkenyl, $C_2$-$C_8$ alkynyl, $C_6$-$C_{20}$ aryl, $C_1$-$C_{20}$ heterocyclyl, or a protecting group selected from a trialkylsilyl, a dialkylphenylsilyl, benzoate, benzyl, benzyloxymethyl, methyl, methoxymethyl, a triarylmethyl, phthalimido and tetrahydropyranyl;
Y is independently O, S, NR, N$^+$(O)(R), N(OR), N$^+$(O)(OR), or N-N(R)$_2$; and
n is 1, 2, 3, 4, 5, 6, 7, or 8.

3. The compound of claim 1 wherein $R^2$ is H.

4. The compound of claim 1 wherein $R^2$ is methyl.

5. The compound of claim 1 wherein $R^3$ is hydrogen.

6. The compound of claim 1 wherein $R^4$ and $R^5$ are each hydrogen.

7. The compound of claim 1 wherein the carbon atom bearing $R^3$ is in the R configuration.

8. The compound of claim 1 wherein the carbon atom bearing $R^3$ is in the S configuration.

9. The compound of claim 1 wherein the carbon atom bearing the boron atom is in the R configuration.

10. The compound of claim 1 wherein the carbon atom bearing the boron atom is in the S configuration.

11. The compound of claim 1 wherein R is a protecting group selected from a trialkylsilyl, a dialkylphenylsilyl, benzoate, benzyl, benzyloxymethyl, methyl, methoxymethyl, a triarylmethyl, phthalimido and tetrahydropyranyl.

12. A compound selected from the structures:

-continued
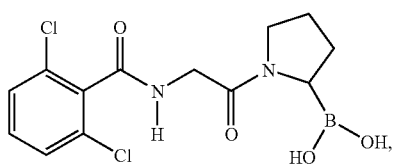
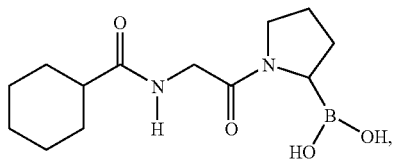
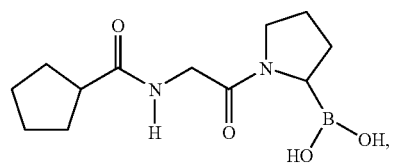
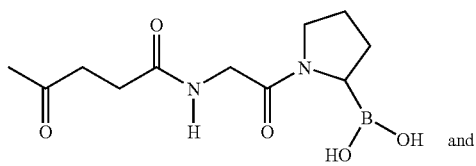
and
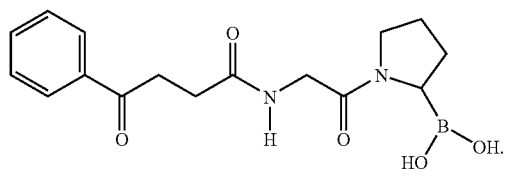
13. A compound selected from the structures:
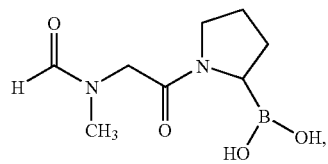
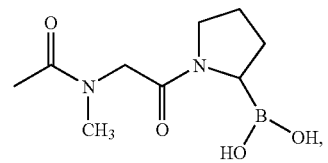
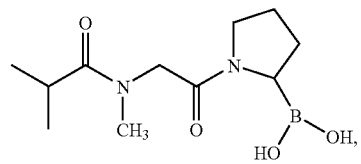
-continued
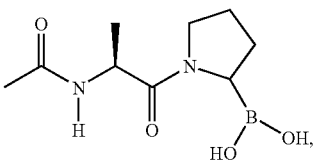
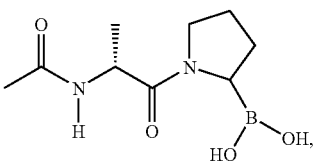
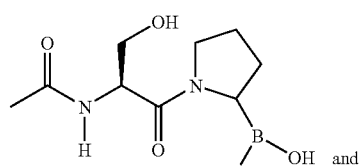
and
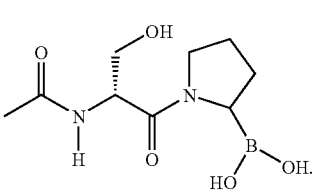
14. A compound selected from the structures:
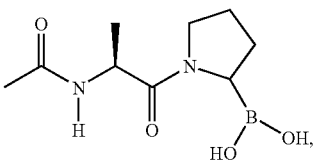

15. A compound of the structure:

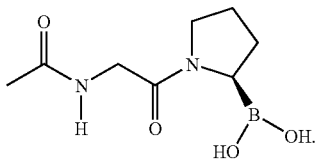

16. The compound of claim 2 wherein $R^2$ is H.
17. The compound of claim 2 wherein at least one of $R^2$ is methyl.
18. The compound of claim 2 wherein $R^4$ and $R^5$ are each H.
19. A compound selected from the structures:

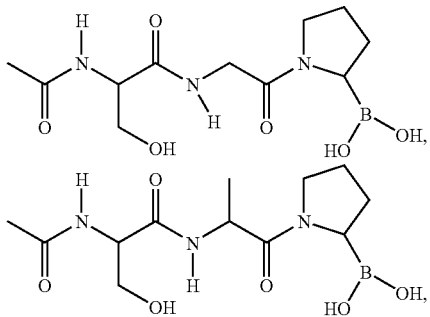

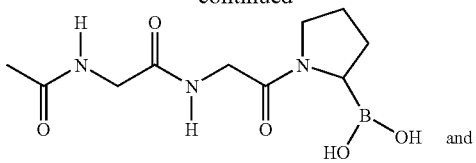

20. A composition comprising the compound according to claim 1 or claim 2 in an amount to inhibit FAP activity in vitro, and a pharmaceutically acceptable carrier, adjuvant, or vehicle.

21. A composition comprising the compound according to claim 1 or claim 2 in an amount to inhibit POP activity in vitro, and a pharmaceutically acceptable carrier, adjuvant, or vehicle.

* * * * *